(12) United States Patent
Uzgiris et al.

(10) Patent No.: US 8,119,349 B2
(45) Date of Patent: Feb. 21, 2012

(54) METHODS AND MATERIALS FOR DETECTING MUTATIONS IN QUASISPECIES HAVING LENGTH POLYMORPHISMS

(75) Inventors: Arejas Uzgiris, Berkeley, CA (US); Sharon Kemp, Cambridge (GB)

(73) Assignee: Siemens Healthcare Diagnostics, Inc., Tarrytown, NY (US)

( * ) Notice: Subject to any disclaimer, the term of this patent is extended or adjusted under 35 U.S.C. 154(b) by 0 days.

(21) Appl. No.: 12/902,325

(22) Filed: Oct. 12, 2010

(65) Prior Publication Data

US 2011/0020791 A1 Jan. 27, 2011

Related U.S. Application Data

(63) Continuation of application No. 11/207,526, filed on Aug. 19, 2005, now abandoned.

(60) Provisional application No. 60/603,195, filed on Aug. 20, 2004, provisional application No. 60/603,337, filed on Aug. 20, 2004.

(51) Int. Cl.
*C12Q 1/68* (2006.01)
*C07H 21/04* (2006.01)
(52) U.S. Cl. .................. 435/6.1; 435/975; 536/24.33
(58) Field of Classification Search .................. None
See application file for complete search history.

(56) References Cited

U.S. PATENT DOCUMENTS 4,629,783 A * 12/1986 Cosand .................. 530/324

FOREIGN PATENT DOCUMENTS

WO 03029285 4/2003

OTHER PUBLICATIONS

Buck et al ("Design Strategies and Performance of Custom DNA Sequencing Primers" Biotechniques. 1999. 27(3): pp. 528-536).*
Stratagene ("Gene Characterization Kits" 1988).*
Wei et al., Emergence of resistant human immunodeficiency virus type I in patients receiving fusion inhibitor (t-20) monotherapy, Anitmicrobial Agents and Chemotherapy, 46(6): 1896-1905 (2002).
Eshleman et al., Performance of the Celera Diagnostics Viro-Seq HIV-1 Genotyping System for sequence-based analysis of diverse human immunodeficiency virus type 1 strains, J. of Clin. Microbiology, 42(6): 2711-2717 (2004).
Greenberg et al., Resistance to enfuvirtide, the first HIV fusion inhibitor, The J. of Anitmicrobial Chemotherapy, 54(2): 333-340 (2004).
Kitrinos et al., Turnover of env variable region 1 and 2 genotypes in sujects with late-stage human immuodeficiency virus type 1 infection, J. of Vir., 77(12) 6811-6822 (2003).
Wiemann et al., Simultaneous on-line DNA sequencing on both strands with two fluorescent dyes, Analytical Biochemistry, 224(1): 117-121 (1995).
Van Laethem et al., A genotypic resistance assay for the detection of drug resistance in the human immunodeficiency virus type 1 envelope gene, J. of Virological Methods, 123(1): 25-34 (2005).
Carmona et al., Natural resistance-associated mutations to Enfuvirtide (T20) and polymorphisms in the gp41 region of different HIV-1 genetic forms from T20 naive patients, J. of Clinval Virology, 32(3): 248-253 (2005).
Supplementary EP Search Report for application No. EP05 78 6680.
Gritz et al., J. Virol, 64 (12): 5948-5957 (1990).
Salminen, AIDS research and Human Retroviruses, 8(9): 1733-1742 (1992).
Ayehunie et al., Virus Genes, 5(4): 359-366 (1991).

* cited by examiner

*Primary Examiner* — Christopher M. Babic

(57) ABSTRACT

The present invention is directed to a method for detecting the presence or absence of a mutation of interest in the nucleic acid of a pathogen, wherein the mutation of interest is located adjacent to a length polymorphism defining multiple quasispecies of the pathogen.

12 Claims, No Drawings

SEQUENCE LISTING

<160> NUMBER OF SEQ ID NOS: 35

<210> SEQ ID NO 1
<211> LENGTH: 9181
<212> TYPE: DNA
<213> ORGANISM: Human immunodeficiency virus type 1

<400> SEQUENCE: 1

```
ggtctctctg gttagaccag atctgagcct gggagctctc tggctaacta gggaacccac      60
tgcttaagcc tcaataaagc ttgccttgag tgcttcaagt agtgtgtgcc cgtctgttgt     120
gtgactctgg taactagaga tccctcagac ccttttagtc agtgtggaaa atctctagca     180
gtggcgcccg aacagggacc tgaaagcgaa agggaaacca gaggagctct ctcgacgcag     240
gactcggctt gctgaagcgc gcacggcaag aggcgagggg cggcgactgg tgagtacgcc     300
aaaaattttg actagcggag gctagaagga gagagatggg tgcgagagcg tcagtattaa     360
gcgggggaga attagatcga tgggaaaaaa ttcggttaag ccaggggga  aagaaaaat     420
ataaattaaa acatatagta tgggcaagca gggagctaga acgattcgca gttaatcctg     480
gcctgttaga acatcagaa ggctgtagac aaatactggg acagctacaa ccatcccttc     540
agacaggatc agaagaactt agatcattat ataatacagt agcaaccctc tattgtgtgc     600
atcaaaggat agagataaaa gacaccaagg aagctttaga caagatagag gaagagcaaa     660
acaaaagtaa gaaaaaagca cagcaagcag cagctgacac aggacacagc aatcaggtca     720
gccaaaatta ccctatagtg cagaacatcc aggggcaaat ggtacatcag gccatatcac     780
ctagaacttt aaatgcatgg gtaaaagtag tagaagagaa ggctttcagc ccagaagtga     840
tacccatgtt ttcagcatta tcagaaggag ccaccccaca gatttaaac  accatgctaa     900
acacagtggg gggacatcaa gcagccatgc aaatgttaaa agagaccatc aatgaggaag     960
ctgcagaatg gatagagtg catccagtgc atgcagggcc tattgcacca ggccagatga    1020
gagaaccaag gggaagtgac atagcaggaa ctactagtac ccttcaggaa caaataggat    1080
ggatgacaaa taatccacct atcccagtag gagaaattta taaagatgg  ataatcctgg    1140
gattaaataa aatagtaaga atgtatagcc ctaccagcat tctggacata agacaaggac    1200
caaaggaacc ctttagagac tatgtagacc ggttctataa aactctaaga gccgagcaag    1260
cttcacagga ggtaaaaaat tggatgacag aaaccttgtt ggtccaaaat gcgaacccag    1320
attgtaagac tattttaaaa gcattgggac cagcggctac actagaagaa atgatgacag    1380
catgtcaggg agtaggagga cccggccata aggcaagagt tttggctgaa gcaatgagcc    1440
aagtaacaaa ttcagctacc ataatgatgc agagaggcaa ttttaggaac caaagaaaga    1500
ttgttaagtg tttcaattgt ggcaaagaag ggcacacagc cagaaattgc agggccccta    1560
ggaaaaaggg ctgttggaaa tgtggaaagg aaggacacca atgaaagat  tgtactgaga    1620
gacaggctaa ttttttaggg aagatctggc cttcctacaa gggaaggcca gggaattttc    1680
ttcagagcag accagagcca acagccccac cagaagagag cttcaggtct ggggtagaga    1740
caacaactcc ccctcagaag caggagccga tagacaagga actgtatcct ttaacttccc    1800
tcaggtcact ctttggcaac gacccctcgt cacaataaag ataggggggc aactaaagga    1860
agctctatta gatacaggag cagatgatac agtattagaa gaaatgagtt tgccaggaag    1920
atggaaacca aaaatgatag ggggaattgg aggttttatc aaagtaagac agtatgatca    1980
gatactcata gaaatctgtg gacataaagc tataggtaca gtattagtag gacctacacc    2040
```

```
tgtcaacata attggaagaa atctgttgac tcagattggt tgcactttaa attttcccat      2100
tagccctatt gagactgtac cagtaaaatt aaagccagga atggatgcc caaaagttaa       2160 acaatggcca ttgacagaag aaaaaataaa agcattagta gaaatttgta cagagatgga     2220
aaaggaaggg aaaatttcaa aaattgggcc tgaaaatcca tacaatactc cagtatttgc     2280
cataaagaaa aaagacagta ctaaatggag aaaattagta gatttcagag aacttaataa     2340
gagaactcaa gacttctggg aagttcaatt aggaatacca catcccgcag ggttaaaaaa    2400
gaaaaaatca gtaacagtac tggatgtggg tgatgcatat ttttcagttc ccttagatga    2460
agacttcagg aagtatactg catttaccat acctagtata aacaatgaga caccagggat     2520
tagatatcag tacaatgtgc ttccacaggg atggaaagga tcaccagcaa tattccaaag    2580
tagcatgaca aaaatcttag agccttttag aaaacaaaat ccagacatag ttatctatca    2640
atacatggat gatttgtatg taggatctga cttagaaata gggcagcata gaacaaaaat    2700
agaggagctg agacaacatc tgttgaggtg gggacttacc acaccagaca aaaaacatca    2760
gaaagaacct ccattccttt ggatgggtta tgaactccat cctgataaat ggacagtaca    2820
gcctatagtg ctgccagaaa aagacagctg gactgtcaat gacatacaga agttagtggg    2880
gaaattgaat tgggcaagtc agatttaccc agggattaaa gtaaggcaat tatgtaaact    2940
ccttagagga accaaagcac taacagaagt aataccacta acagaagaag cagagctaga    3000
actggcagaa aacagagaga ttctaaaaga accagtacat ggagtgtatt atgacccatc    3060
aaaagactta atagcagaaa tacagaagca ggggcaaggc caatggacat atcaaattta    3120
tcaagagcca tttaaaaatc tgaaaacagg aaaatatgca agaatgaggg gtgcccacac    3180
taatgatgta aaacaattaa cagaggcagt gcaaaaaata accacagaaa gcatagtaat    3240
atggggaaag actcctaaat ttaaactgcc catacaaaag gaaacatggg aaacatggtg    3300
gacagagtat tggcaagcca cctggattcc tgagtgggag tttgttaata cccctccctt    3360
agtgaaatta tggtaccagt tagagaaaga acccatagta ggagcagaaa ccttctatgt    3420
agatggggca gctaacaggg agactaaatt aggaaaagca ggatatgtta ctaatagagg    3480
aagacaaaaa gttgtcaccc taactgacac aacaaatcag aagactgagt tacaagcaat    3540
ttatctagct ttgcaggatt cgggattaga agtaaacata gtaacagact cacaatatgc    3600
attaggaatc attcaagcac aaccagatca aagtgaatca gagttagtca atcaaataat    3660
agagcagtta ataaaaaagg aaaaggtcta tctggcatgg gtaccagcac acaaaggaat    3720
tggaggaaat gaacaagtag ataaattagt cagtgctgga atcaggaaag tactattttt    3780
agatggaata gataaggccc aagatgaaca tgagaaatat cacagtaatt ggagagcaat    3840
ggctagtgat tttaacctgc cacctgtagt agcaaaagaa atagtagcca gctgtgataa    3900
atgtcagcta aaaggagaag ccatgcatgg acaagtagac tgtagtccag gaatatggca    3960
actagattgt acacatttag aaggaaaagt tatcctggta gcagttcatg tagccagtgg    4020
atatatagaa gcagaagtta ttccagcaga acagggcag gaaacagcat attttctttt    4080
aaaattagca ggaagatggc cagtaaaaac aatacatact gacaatggca gcaatttcac    4140
cggtgctacg gttagggccg cctgttggtg gcgggaatc aagcaggaat ttggaattcc    4200
ctacaatccc caaagtcaag gagtagtaga atctatgaat aaagaattaa agaaaattat    4260
aggacaggta agagatcagg ctgaacatct taagacagca gtacaaatgg cagtattcat    4320
ccacaatttt aaaagaaaag gggggattgg ggggtacagt gcaggggaaa gaatagtaga    4380
cataatagca acagacatac aaactaaaga attacaaaaa caaattacaa aaattcaaaa    4440
```

```
ttttcgggtt tattacaggg acagcagaaa tccactttgg aaaggaccag caaagctcct    4500
ctggaaaggt gaaggggcag tagtaataca agataatagt gacataaaag tagtgccaag    4560
aagaaaagca aagatcatta gggattatgg aaaacagatg gcaggtgatg attgtgtggc    4620
aagtagacag gatgaggatt agaacatgga aaagtttagt aaaacaccat atgtatgttt    4680
cagggaaagc taggggatgg ttttatagac atcactatga aagccctcat ccaagaataa    4740
gttcagaagt acacatccca ctaggggatg ctagattggt aataacaaca tattggggtc    4800
tgcatacagg agaaagagac tggcatttgg gtcagggagt ctccatagaa tggaggaaaa    4860
agagatatag cacacaagta gaccctgaac tagcagacca actaattcat ctgtattact    4920
ttgactgttt ttcagactct gctataagaa aggccttatt aggacacata gttagcccta    4980
ggtgtgaata tcaagcagga cataacaagg taggatctct acaatacttg gcactagcag    5040
cattaataac accaaaaaag ataaagccac ctttgcctag tgttacgaaa ctgacagagg    5100
atagatggaa caagccccag aagaccaagg gccacagagg gagccacaca atgaatggac    5160
actagagctt ttagaggagc ttaagaatga agctgttaga cattttccta ggatttggct    5220
ccatggctta gggcaacata tctatgaaac ttatggggat acttgggcag gagtggaagc    5280
cataataaga attctgcaac aactgctgtt tatccatttt cagaattggg tgtcgacata    5340
gcagaatagg cgttactcga cagaggagag caagaaatgg agccagtaga tcctagacta    5400
gagccctgga agcatccagg aagtcagcct aaaactgctt gtaccaattg ctattgtaaa    5460
aagtgttgct ttcattgcca gtttgtttc ataacaaaag ccttaggcat ctcctatggc    5520
aggaagaagc ggagacagcg acgaagagct catcagaaca gtcagactca tcaagcttct    5580
ctatcaaagc agtaagtagt acatgtaatg caacctatac caatagtagc aatagtagca    5640
ttagtagtag caataataat agcaatagtt gtgtggtcca tagtaatcat agaatatagg    5700
aaaatattaa gacaaagaaa atagacagg ttaattgata gactaataga aagagcagaa    5760
gacagtggca atgagagtga aggagaaata tcagcacttg tggagatggg ggtggagatg    5820
gggcaccatg ctccttggga tgttgatgat ctgtagtgct acagaaaaat tgtgggtcac    5880
agtctattat ggggtacctg tgtggaagga agcaaccacc actctatttt gtgcatcaga    5940
tgctaaagca tatgatacag aggtacataa tgtttgggcc acacatgcct gtgtacccac    6000
agaccccaac ccacaagaag tagtattggt aaatgtgaca gaaaatttta acatgtggaa    6060
aaatgacatg gtagaacaga tgcatgagga tataatcagt ttatgggatc aaagcctaaa    6120
gccatgtgta aaattaaccc cactctgtgt tagtttaaag tgcactgatt tgaagaatga    6180
tactaatacc aatagtagta gcgggagaat gataatggag aaaggagaga taaaaaactg    6240
ctctttcaat atcagcacaa gcataagagg taaggtgcag aaagaatatg catttttta    6300 taaacttgat ataataccaa tagataatga tactaccagc tataagttga caagttgtaa    6360
cacctcagtc attacacagg cctgtccaaa ggtatccttt gagccaattc ccatacatta    6420
ttgtgccccg gctggttttg cgattctaaa atgtaataat aagacgttca atggaacagg    6480
accatgtaca aatgtcagca cagtacaatg tacacatgga attaggccag tagtatcaac    6540
tcaactgctg ttaaatggca gtctagcaga agaagaggta gtaattagat ctgtcaattt    6600
cacggacaat gctaaaacca taatagtaca gctgaacaca tctgtagaaa ttaattgtac    6660
aagacccaac aacaatacaa gaaaagaat ccgtatccag agaggaccag ggagagcatt    6720
tgttacaata ggaaaatag gaaatatgag acaagcacat tgtaacatta gtagagcaaa    6780
atggaataac actttaaaac agatagctag caaattaaga gaacaatttg gaaataataa    6840
```

```
aacaataatc tttaagcaat cctcaggagg ggacccagaa attgtaacgc acagttttaa    6900
ttgtggaggg gaattttttct actgtaattc aacacaactg tttaatagta cttggtttaa   6960
tagtacttgg agtactgaag ggtcaaataa cactgaagga agtgacacaa tcaccctccc    7020
atgcagaata aaacaaatta taaacatgtg gcagaaagta ggaaaagcaa tgtatgcccc    7080
tcccatcagt ggacaaatta gatgttcatc aaatattaca gggctgctat taacaagaga   7140
tggtggtaat agcaacaatg agtccgagat cttcagacct ggaggaggag atatgaggga   7200
caattggaga agtgaattat ataaatataa agtagtaaaa attgaaccat taggagtagc   7260
acccaccaag gcaaagagaa gagtggtgca gagagaaaaa agagcagtgg gaataggagc   7320
tttgttcctt gggttcttgg gagcagcagg aagcactatg ggcgcagcct caatgacgct   7380
gacggtacag gccagacaat tattgtctgg tatagtgcag cagcagaaca atttgctgag   7440
ggctattgag gcgcaacagc atctgttgca actcacagtc tggggcatca agcagctcca   7500
ggcaagaatc ctggctgtgg aaagatacct aaaggatcaa cagctcctgg ggatttgggg   7560
ttgctctgga aaactcattt gcaccactgc tgtgccttgg aatgctagtt ggagtaataa   7620
atctctggaa cagatttgga atcacacgac ctggatggag tgggacagag aaattaacaa   7680
ttacacaagc ttaatacact ccttaattga agaatcgcaa aaccagcaag aaaagaatga   7740
acaagaatta ttggaattag ataaatgggc aagtttgtgg aattggttta acataacaaa   7800
ttggctgtgg tatataaaat tattcataat gatagtagga ggcttggtag gtttaagaat   7860
agtttttgct gtactttcta tagtgaatag agttaggcag ggatattcac cattatcgtt   7920
tcagacccac ctcccaaccc cgaggggacc cgacaggccc gaaggaatag aagaagaagg   7980
tggagagaga gacagagaca gatccattcg attagtgaac ggatccttgg cacttatctg   8040
ggacgatctg cggagcctgt gcctcttcag ctaccaccgc ttgagagact tactcttgat   8100
tgtaacgagg attgtggaac ttctgggacg caggggtgg gaagccctca aatattggtg    8160
gaatctccta cagtattgga gtcaggaact aaagaatagt gctgttagct tgctcaatgc   8220
cacagccata gcagtagctg aggggacaga taggtttata gaagtagtac aaggagcttg   8280
tagagctatt cgccacatac ctagaagaat aagacagggc ttggaaagga ttttgctata   8340
agatgggtgg caagtggtca aaaagtagtg tgattggatg gcctactgta agggaaagaa   8400
tgagacgagc tgagccagca gcagataggg tgggagcagc atctcgagac ctggaaaaac   8460
atggagcaat cacaagtagc aatacagcag ctaccaatgc tgcttgtgcc tggctagaag   8520
cacaagagga ggaggaggtg ggttttccag tcacacctca ggtaccttta agaccaatga   8580
cttacaaggc agctgtagat cttagccact ttttaaaaga aaagggggga ctggaagggc   8640
taattcactc ccaaagaaga caagatatcc ttgatctgtg gatctaccac acacaaggct   8700
acttccctga ttagcagaac tacacaccag ggccagggt cagatatcca ctgacctttg   8760
gatggtgcta caagctagta ccagttgagc cagataagat agaagaggcc aataaaggag   8820
agaacaccag cttgttacac cctgtgagcc tgcatggat ggatgacccg gagagagaag    8880
tgttagagtg gaggtttgac agccgcctag catttcatca cgtggcccga gagctgcatc   8940
cggagtactt caagaactgc tgacatcgag cttgctacaa gggactttcc gctggggact   9000
ttccagggag gcgtggcctg gcgggactg gggagtggcg agccctcaga tcctgcatat   9060
aagcagctgc ttttttgcctg tactgggtct ctctggttag accagatctg agcctgggag   9120
ctctctggct aactagggaa cccactgctt aagcctcaat aaagcttgcc ttgagtgctt   9180
c                                                                    9181
```

```
<210> SEQ ID NO 2
<211> LENGTH: 28
<212> TYPE: DNA
<213> ORGANISM: Human immunodeficiency virus type 1
<220> FEATURE:
<221> NAME/KEY: misc_feature
<222> LOCATION: (6)..(6)
<223> OTHER INFORMATION: n is a, c, g, or t

<400> SEQUENCE: 2
gcaccnacsa rggcaaagag amgagygg                                          28

<210> SEQ ID NO 3
<211> LENGTH: 22
<212> TYPE: DNA
<213> ORGANISM: Human immunodeficiency virus type 1

<400> SEQUENCE: 3
accaaggcaa agagaagagt gg                                                22

<210> SEQ ID NO 4
<211> LENGTH: 25
<212> TYPE: DNA
<213> ORGANISM: Human immunodeficiency virus type 1

<400> SEQUENCE: 4
cccaccaagg caaagagaag agtgg                                             25

<210> SEQ ID NO 5
<211> LENGTH: 28
<212> TYPE: DNA
<213> ORGANISM: Human immunodeficiency virus type 1

<400> SEQUENCE: 5
gcacccacca aggcaaagag aagagtgg                                          28

<210> SEQ ID NO 6
<211> LENGTH: 28
<212> TYPE: DNA
<213> ORGANISM: Human immunodeficiency virus type 1

<400> SEQUENCE: 6
gcacccacca aggcaaagag aagagygg                                          28

<210> SEQ ID NO 7
<211> LENGTH: 28
<212> TYPE: DNA
<213> ORGANISM: Human immunodeficiency virus type 1

<400> SEQUENCE: 7
gcacccacca aggcaaagag amgagygg                                          28

<210> SEQ ID NO 8
<211> LENGTH: 28
<212> TYPE: DNA
<213> ORGANISM: Human immunodeficiency virus type 1

<400> SEQUENCE: 8
gcacccacca gggcaaagag amgagygg                                          28

<210> SEQ ID NO 9
<211> LENGTH: 28
<212> TYPE: DNA
<213> ORGANISM: Human immunodeficiency virus type 1
```

```
<400> SEQUENCE: 9
gcacccacga gggcaaagag amgagygg                                              28

<210> SEQ ID NO 10
<211> LENGTH: 28
<212> TYPE: DNA
<213> ORGANISM: Human immunodeficiency virus type 1
<220> FEATURE:
<221> NAME/KEY: misc_feature
<222> LOCATION: (6)..(6)
<223> OTHER INFORMATION: n is a, c, g, or t

<400> SEQUENCE: 10
gcaccnacga gggcaaagag amgagygg                                              28

<210> SEQ ID NO 11
<211> LENGTH: 22
<212> TYPE: DNA
<213> ORGANISM: Human immunodeficiency virus type 1

<400> SEQUENCE: 11
acgagggcaa agagamgagy gg                                                    22

<210> SEQ ID NO 12
<211> LENGTH: 20
<212> TYPE: DNA
<213> ORGANISM: Human immunodeficiency virus type 1

<400> SEQUENCE: 12
ccaaggcaaa gagaagagtg                                                       20

<210> SEQ ID NO 13
<211> LENGTH: 20
<212> TYPE: DNA
<213> ORGANISM: Human immunodeficiency virus type 1

<400> SEQUENCE: 13
cgagggcaaa gagamgagyg                                                       20

<210> SEQ ID NO 14
<211> LENGTH: 28
<212> TYPE: DNA
<213> ORGANISM: Human immunodeficiency virus type 1

<400> SEQUENCE: 14
gcacccacca aggcaaagag aagagtgg                                              28

<210> SEQ ID NO 15
<211> LENGTH: 22
<212> TYPE: DNA
<213> ORGANISM: Human immunodeficiency virus type 1

<400> SEQUENCE: 15
accaaggcaa agagaagagt gg                                                    22

<210> SEQ ID NO 16
<211> LENGTH: 29
<212> TYPE: DNA
<213> ORGANISM: Human immunodeficiency virus type 1
<220> FEATURE:
<221> NAME/KEY: misc_feature
<222> LOCATION: (11)..(11)
<220> FEATURE:
<221> NAME/KEY: misc_feature
<222> LOCATION: (11)..(11)
<223> OTHER INFORMATION: n is a, c, g, or t
```

```
<220> FEATURE:
<221> NAME/KEY: misc_feature
<222> LOCATION: (20)..(20)
<223> OTHER INFORMATION: n is a, c, g, or t

<400> SEQUENCE: 16
tartaggagg nttrataggn ttaagaata                                            29

<210> SEQ ID NO 17
<211> LENGTH: 23
<212> TYPE: DNA
<213> ORGANISM: Human immunodeficiency virus type 1

<400> SEQUENCE: 17
gtaggaggct tgataggttt aag                                                  23

<210> SEQ ID NO 18
<211> LENGTH: 25
<212> TYPE: DNA
<213> ORGANISM: Human immunodeficiency virus type 1

<400> SEQUENCE: 18
tagtaggagg cttgataggt ttaag                                                25

<210> SEQ ID NO 19
<211> LENGTH: 25
<212> TYPE: DNA
<213> ORGANISM: Human immunodeficiency virus type 1

<400> SEQUENCE: 19
tartaggagg cttgataggt ttaag                                                25

<210> SEQ ID NO 20
<211> LENGTH: 25
<212> TYPE: DNA
<213> ORGANISM: Human immunodeficiency virus type 1
<220> FEATURE:
<221> NAME/KEY: misc_feature
<222> LOCATION: (11)..(11)
<223> OTHER INFORMATION: n is a, c, g, or t

<400> SEQUENCE: 20
tartaggagg nttgataggt ttaag                                                25

<210> SEQ ID NO 21
<211> LENGTH: 25
<212> TYPE: DNA
<213> ORGANISM: Human immunodeficiency virus type 1
<220> FEATURE:
<221> NAME/KEY: misc_feature
<222> LOCATION: (11)..(11)
<223> OTHER INFORMATION: n is a, c, g, or t

<400> SEQUENCE: 21
tartaggagg nttrataggt ttaag                                                25

<210> SEQ ID NO 22
<211> LENGTH: 25
<212> TYPE: DNA
<213> ORGANISM: Human immunodeficiency virus type 1
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
```

```
<400> SEQUENCE: 22
tartaggagg nttrataggn ttaag                                          25

<210> SEQ ID NO 23
<211> LENGTH: 29
<212> TYPE: DNA
<213> ORGANISM: Human immunodeficiency virus type 1
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 23
tartaggagg nttrataggn ttaagaata                                      29

<210> SEQ ID NO 24
<211> LENGTH: 24
<212> TYPE: DNA
<213> ORGANISM: Human immunodeficiency virus type 1
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 24
ggaggnttra taggnttaag aata                                           24

<210> SEQ ID NO 25
<211> LENGTH: 24
<212> TYPE: DNA
<213> ORGANISM: Human immunodeficiency virus type 1
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 25
ggvggnttra taggnttaag aata                                           24

<210> SEQ ID NO 26
<211> LENGTH: 22
<212> TYPE: DNA
<213> ORGANISM: Human immunodeficiency virus type 1
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 26
taggaggntt rataggntta ag                                             22

<210> SEQ ID NO 27
<211> LENGTH: 21
```

```
<212> TYPE: DNA
<213> ORGANISM: Human immunodeficiency virus type 1

<400> SEQUENCE: 27
ggaggcttgg taggtttaag a                                              21

<210> SEQ ID NO 28
<211> LENGTH: 21
<212> TYPE: DNA
<213> ORGANISM: Human immunodeficiency virus type 1
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 28
ggvggnttra taggnttaag a                                              21

<210> SEQ ID NO 29
<211> LENGTH: 29
<212> TYPE: DNA
<213> ORGANISM: Human immunodeficiency virus type 1

<400> SEQUENCE: 29
tagtaggagg cttgataggt ttaagaata                                      29

<210> SEQ ID NO 30
<211> LENGTH: 23
<212> TYPE: DNA
<213> ORGANISM: Human immunodeficiency virus type 1

<400> SEQUENCE: 30
gtaggaggct tgataggttt aag                                            23

<210> SEQ ID NO 31
<211> LENGTH: 25
<212> TYPE: DNA
<213> ORGANISM: Human immunodeficiency virus type 1

<400> SEQUENCE: 31
ttgggttctt gggagcagca ggaag                                          25

<210> SEQ ID NO 32
<211> LENGTH: 22
<212> TYPE: DNA
<213> ORGANISM: Human immunodeficiency virus type 1

<400> SEQUENCE: 32
ttgggttctt gggagcagca gg                                             22

<210> SEQ ID NO 33
<211> LENGTH: 25
<212> TYPE: DNA
<213> ORGANISM: Human immunodeficiency virus type 1

<400> SEQUENCE: 33
agtrgtgcar atgaktttc cagag                                           25

<210> SEQ ID NO 34
<211> LENGTH: 24
<212> TYPE: DNA
<213> ORGANISM: Human immunodeficiency virus type 1
```

```
<400> SEQUENCE: 34
gtggtgcaga tgagttttcc agag                                            24

<210> SEQ ID NO 35
<211> LENGTH: 25
<212> TYPE: DNA
<213> ORGANISM: Human immunodeficiency virus type 1

<400> SEQUENCE: 35
gtggtgcaga tgagttttcc agagc                                           25
```

METHODS AND MATERIALS FOR DETECTING MUTATIONS IN QUASISPECIES HAVING LENGTH POLYMORPHISMS

CROSS-REFERENCE TO RELATED APPLICATIONS

This application claims the benefit of U.S. Provisional Application No. 60/603,195, filed Aug. 20, 2004, and U.S. Provisional Application No. 60/603,337, filed Aug. 20, 2004.

BACKGROUND OF THE INVENTION

The present invention generally relates to methods and materials for detecting the presence or absence of a mutation of interest in a pathogen. The present invention also relates to particular methods and primers for determining the presence or absence of a mutation among multiple human immunodeficiency virus (HIV-1) quasispecies present in a sample from a single patient.

The nucleic acid sequence of pathogens are often subject to a high mutation rate, giving rise to a variety of polymorphic variants. For example, human immunodeficiency virus, a member of the Lentivirus group of retroviruses, and the primary causative agent of Acquired Immune Deficiency Syndrome (AIDS), or AIDS-related complex (ARC), typically undergoes frequent mutation. The HIV-1 RNA genome comprises various genes that encode proteins necessary for the replication of HIV-1. Like all other retroviruses, it has an RNA genome which is replicated by means of the viral reverse transcriptase (RT) enzyme, which copies the single-stranded viral RNA genome into a double-stranded DNA/RNA hybrid, resulting in integration of the DNA provirus into the host cell genome. The RT enzyme lacks a 3'exonuclease activity which normally helps the "proof-reading" function of a polymerase enzyme to repair errors. Consequently, the RT enzyme makes at least one error during every transcription of 10,000 bases copied, resulting in errors that are responsible for the high mutation rate of HIV-1.

The HIV-1 RNA genome also includes a gene that encodes the envelope glycoprotein (env), which consists of two principle subunits—the gp120 surface glycoprotein and the gp41 transmembrane glycoprotein. The gp41 subunit encodes transmembrane proteins that facilitate fusion of the HIV-1 virus to the outer cell membrane of CD4 cells. Because the HIV-1 env protein plays a critical role in the initial infection of CD4 cells, it has been a primary target in the search for drugs that can inhibit the interaction of proteins responsible for fusion of HIV-1 to cells, thereby inhibiting HIV infection. One particular target in the gp41 subunit of the HIV-1 env protein is the heptad repeat 1 (HR1) and heptad repeat 2 (HR2) domains, which have been shown to play a key role in facilitating the conformational changes required for fusion of viral and cellular membranes. Because many anti-retroviral drugs target the HIV-1 env protein in order to inhibit entry of HIV-1 into the cell, many mutations responsible for HIV-1 drug resistance arise in this region.

Various drugs that are presently available to treat HIV fall into three different classes—nucleoside reverse transcriptase inhibitors (NRTIs), non-nucleoside reverse transcriptase inhibitors (NNRTIs), and protease inhibitors (PIs). Presently available anti-retroviral compounds used to treat AIDS suffer from certain disadvantages, including transient CD4 cell count effects, incomplete inhibition of viral replication, toxicity at prescribing doses, and emergence of resistant forms of the virus. Even with the advent of combination therapies, many patients remain unable to achieve or maintain complete viral suppression even with anti-retroviral compounds. As a result of incomplete viral suppression, coupled with the very high mutagenicity rate of HIV virus (due to the error-prone nature of the viral RT enzyme) and the genetic variability of the virus, many HIV variants with decreased drug susceptibility have arisen. For example, the use of Enfuvirtide (Enf, previously referred to as T-20), the first of a new class of anti-HIV drugs that inhibit fusion of HIV with a host cell, has resulted in the emergence of resistance mutations in the first heptad repeat domain of gp41 (HR1) that have been linked to T-20 treatment failure.

By identifying mutations associated with HIV-1 drug resistance to specific anti-retroviral drugs before therapeutic intervention, the particular course of therapeutic intervention can be optimized by selecting and administering drugs to which the virus is most susceptible. Mutations can be detected by various techniques, the most direct and reliable of which is sequencing of the viral DNA (genotyping). In the case of clinical genotyping, where critical and even life-saving decisions relating to therapeutic intervention are made based on the genotyping results, confirmation of sequencing results by comparison with the sequence of the complementary strand of DNA is even more critical. The effectiveness of genotyping, and the ability to obtain bidirectional confirmation of sequence results is, however, compromised when multiple species of a pathogenic vector are present in a single patient sample. Because a patient sample containing mixed species of a pathogenic vector will contain multiple variants of the DNA sequence, sequencing will show multiple bases at a particular location and, in the case of insertion or deletion mutations, will show multiple bases at each location over an entire region of the DNA as a result of a shift in the reading frame, thus confounding the results and precluding complementary strand confirmation of the sequence and identification of clinically relevant mutations within that sequence. Pathogenic vectors that are present in the form of multiple species within a patient sample have therefore become increasingly refractory to clinical genotyping efforts, and have become a significant challenge to creating diagnostic assays to detect clinically relevant mutations, such as mutations that cause viral resistance to particular therapeutic drugs.

Consequently, there is a need to develop more accurate and reliable genotyping methods that are amenable to complementary strand confirmation in clinical settings, and that are capable of detecting and identifying clinically relevant mutations in a pathogenic vector present in the form of multiple quasispecies within a patient sample.

SUMMARY OF THE INVENTION

The present invention provides improved methods and materials for clinical genotyping of a pathogen, such as HIV, present in a patient sample containing multiple quasispecies of the pathogen.

In a particular aspect, the present invention relates to methods and materials for detecting the presence or absence of a mutation of interest in a pathogen present in a sample containing multiple quasispecies of the pathogen having mixed length polymorphisms, wherein the mutation of interest is located adjacent to the length polymorphism In a particular aspect, the present invention is directed to methods and materials for detecting the presence or absence of a mutation of interest in a patient sample containing mixed quasispecies of a pathogen, wherein the mutation of interest is located adjacent to a predetermined length polymorphism, such as an insertion mutation or a deletion mutation, which results in quasispecies of different nucleic acid sequence lengths. In a particular aspect, the present invention provides methods and primers for improved accuracy in genotyping an HIV-1 virus having length polymorphisms, which may be present in a patient sample containing mixed quasispecies. The improved methods and materials of the present invention may improve therapeutic intervention and treatment of infectious diseases, including, for example, AIDS.

The methods and primers of the present invention were developed as a result of the initial discovery that amplification and sequencing of the entire HIV-1 env gene fails to provide reliable complementary strand confirmatory data necessary to identify and confirm the existence of important drug resistance associated mutations, identification of which is essential to therapeutic intervention. The gp41 region of HIV-1 env gene contains a first heptad repeat domain (HR1) and a second heptad repeat domain (HR2). The region surrounding the first heptad repeat domain (HR1) is subject to frequent insertion or deletion mutations, resulting in mixed HIV-1 populations having drug resistance mutations within the HR1 domain, but also containing multiple quasispecies having length polymorphisms. The presence of mixed length polymorphisms among quasispecies in a single patient sample confounds efforts to obtain confirmatory sequence of the complementary strand with primers covering a larger region, because the mixed length polymorphism mutation that occurs between one of the outer primers and the mutations of interest results in complementary primer extension products having sequences of different lengths in the region between the primers, which in turn results in overlayed and out of frame sequence signals being generated. The method of the present invention improves reliability of genotyping by sequencing the region of the mutation of interest, exclusive of the region containing the length polymorphism. The primer set may be used alone or in conjunction with a secondary primer set that includes the regions of variability to confirm genotypes for samples that cannot be reliably characterized using other sequencing primers.

While the methods of the present invention were developed initially with respect to the HIV-1 gene, such methods are nevertheless applicable to any pathogen having length polymorphisms among multiple quasispecies. Accordingly, the present invention is directed to a method for detecting the presence or absence of a mutation of interest in the nucleic acid of a pathogen, such as HIV-1, wherein the mutation of interest is located adjacent to a length polymorphism defining multiple quasispecies of the pathogen, comprising:
a) obtaining from the patient sample a double-stranded DNA template encompassing the mutation of interest;
b) sequencing a first strand of a region of the DNA template containing the mutation of interest, exclusive of the length polymorphism;
c) sequencing a second strand of a region of the DNA template containing the mutation of interest, exclusive of the length polymorphism; and
d) comparing the sequence of the first strand with the sequence of the second strand to obtain complementary strand confirmation of the sequence of the mutation of interest.

In another aspect, the present invention is directed to a method for detecting the presence or absence of a mutation of interest in the nucleic acid of a pathogen, such as HIV-1, wherein the mutation of interest is located adjacent to a length polymorphism defining multiple quasispecies of the pathogen, comprising:
a) obtaining from the patient sample a double-stranded DNA template encompassing the mutation of interest;
b) amplifying a first region of the DNA template containing both the mutation of interest and the length polymorphism;
c) sequencing a first strand of a region of the DNA template containing the mutation of interest, exclusive of the length polymorphism;
d) sequencing a second strand of a region of the DNA template containing the mutation of interest, exclusive of the length polymorphism; and
e) comparing the sequence of the first strand with the sequence of the second strand to obtain complementary strand confirmation of the sequence of the mutation of interest.

In yet another aspect, the present invention is directed to a method for detecting the presence or absence of a mutation of interest in the nucleic acid of a pathogen, such as HIV-1, wherein the mutation of interest is located adjacent to a length polymorphism defining multiple quasispecies of the pathogen, comprising:
a) obtaining from the patient sample a double-stranded DNA template encompassing the mutation of interest;
b) amplifying a first genetic region of the DNA template comprising the mutation of interest, exclusive of the length polymorphism;
c) sequencing a first strand of a region of the DNA template containing the mutation of interest, exclusive of the length polymorphism;
d) sequencing a second strand of a region of the DNA template containing the mutation of interest, exclusive of the length polymorphism; and
e) comparing the sequence of the first strand with the sequence of the second strand to obtain complementary strand confirmation of the sequence of the mutation of interest.

In a one aspect of the invention, the mutation of interest is located in a region of HIV selected from the group consisting of: gp41 and gp120. In another aspect of the invention, the mutation of interest is located in the HIV-1 envelope glycoprotein gp41. In yet another aspect of the invention, the mutation of interest is located within positions 36-45 gp41. SEQ ID NO:1 provides a consensus nucleotide sequence of the complete genomic sequence of human immunodeficiency virus-1 (nucleotides 1-9181). The env region consists of nucleotides 5771-8341. The gp120 region consists of nucleotides 5855-7303. The gp41 region consists of nucleotides 7304-8338. The HR1 region consists of nucleotides 7388-7549. The HR2 region consists of nucleotides 7652-7789.

In another aspect, the present invention is directed to an oligonucleotide primer capable of generating primer extension products corresponding to the region consisting essentially of nucleotides 7329-7614 of SEQ ID NO:1, 7388-7549 of SEQ ID NO:1 or 7492-7522 of SEQ ID NO:1, fragments thereof of 15 or more nucleotides.

In another aspect, the present invention is directed to a combination of forward and reverse primers, selected from the group consisting of SEQ ID NO:31, SEQ ID NO:32, SEQ ID NO:33, SEQ ID NO:34, SEQ ID NO:35 and fragments thereof of 15 or more nucleotides.

In one aspect, the present invention is directed to a method and primers for genotyping the gp41 subunit of the HIV-1 env protein, which comprises determining the sequence of a region encompassing both the HR1 and HR2 domains of the gp41 subunit of the HIV-1 env protein.

In another aspect, the present invention includes primers selected from the group consisting of one or more of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, and fragments thereof of 15 or more nucleotides.

In another aspect, the present invention is directed to a primer combination comprising a set of bi-directional sequencing primers encompassing a region encompassing the HR1 and HR2 domains of HIV-1, wherein the primer combination comprises:

(a) a forward primer selected from the group consisting of one or more of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, and fragments thereof of 15 or more nucleotides; and (b) a reverse primer selected from the group consisting of one or more of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, and fragments thereof of 15 or more nucleotides.

The selected primers, one or more from each group, can be used as reverse transcription, amplification and sequencing primers.

The primers are packaged in a suitable genotyping kit. Such a kit may include reagents in addition to the primers, such as an RNase inhibitor, a reverse transcriptase, a polymerase, and/or DNTP and ddNTP feedstocks. In a preferred aspect, the present invention is directed to a kit for detecting the presence or absence of a mutation of interest in the nucleic acid of a pathogen, wherein the mutation of interest is located adjacent to a length polymorphism defining multiple quasispecies of the pathogen, comprising a first primer for sequencing a first strand of a region of a DNA template containing the mutation of interest and a second primer for sequencing a second strand of a region of the DNA template containing the mutation of interest, wherein the region defined by the first primer and second primer excludes the length polymorphism.

The primers are employed in the method of the invention, as appropriate. In accordance with this method, a sample suspected of containing the HIV-1 virus is treated to recover viral RNA. The recovered viral RNA is reverse transcribed to DNA, which is sequenced using the primers of the invention. The resulting sequence information is used to establish the genotype of the tested virus, i.e., to determine to which subtype, species or quasispecies the virus in the sample belongs, or to determine the presence or absence of the mutation of interest. The method of the invention may be practiced in parallel with genotyping procedures that are designed to evaluate multiple viral species. Alternatively, the method of the invention is practiced on samples that have previously been the subject of a failed attempt to obtain reliable sequence information for the purpose of genotyping the infectious pathogen.

DETAILED DESCRIPTION OF THE INVENTION

While the terminology used in this application is standard within the art, the following definitions of certain terms are provided to assure clarity.

Units, prefixes, and symbols may be denoted in their SI accepted form. Unless otherwise indicated, nucleic acids are written left to right in 5' to 3' orientation. Numeric ranges recited herein are inclusive of the numbers defining the range and include and are supportive of each integer within the defined range. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes. Unless otherwise noted, the terms "a" or "an" are to be construed as meaning "at least one of" The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. In the case of any amino acid or nucleic sequence discrepancy within the application, the figures control.

As used herein, the term "pathogen" means an infectious agent or exogenous vector that originates or is initially produced outside of, but is present in a host organism, such as a viral, bacterial, fungal or protozoan organisms. The method and reagents of the present invention are advantageously used to genotype a pathogen that is present in the host organism in the form of multiple quasispecies, wherein the quasispecies are characterized by having one or more alleles of a length polymorphism that give rise to length polymorphisms among the quasispecies.

As used herein, the term "quasispecies" means a species of self-replicating organism that contains a different genetic sequence as a result of the incorporation or deletion of alternative or additional gene sequences, either correct or erroneous. Quasispecies may result, for example, from the genetic copy process of other gene sequences that are already present. Quasispecies typically arise in the context of the evolutionary processes of self-replicating macromolecules such as RNA or DNA of organisms, such as infectious pathogens, including bacteria and viruses. As used herein, the term "quasispecies" includes both the variant species and the wild-type species from which the variant species was derived.

As used herein, the term "length polymorphism" means any mutation in the genetic sequence that results in a quasispecies having nucleic acid sequence of a different length. Length polymorphism include, but are not limited to, for example, insertion mutations, deletion mutations, and substitution mutations that result in a different nucleic acid sequence length. In automated sequencing of samples containing multiple quasispecies, the sequencing trace will include data from two different sequences (i.e., the reference sequence and the sequence containing the length polymorphism), resulting in multiple peaks being superimposed at a given nucleotide base position. In the context of the present invention, the phrase "length polymorphism defining multiple quasispecies of a pathogen" means the genetic locus with respect to which there exists length polymorphisms that result in multiple quasispecies of the pathogen. Length polymorphisms refer to the various alleles or species of a pathogen that result in different quasispecies, and include the "wild-type" or "reference" species with respect to which the length polymorphism is defined.

As used herein, the term "adjacent" is used in reference to the location of the mutation of interest relative to a length polymorphism. A mutation of interest is considered to be "adjacent" to a length polymorphism when its location is sufficiently proximate that standard amplification and/or sequencing primers encompasses both the mutation of interest and the length polymorphism. While the precise distance between the mutation of interest and the length polymorphism is not critical, any mixed length polymorphism mutation that occurs between one of the outer primers and the mutations of interest causes the sequence quality to decline due to overlayed and out of frame sequences being generated. The methods and materials of the present invention are advantageously employed when primers are utilized that can exclude any or all length polymorphism(s) that generate such overlayed and out of frame sequences.

As used herein, the term "sample" refers to a biological sample obtained from a patient or group of patients that may contain a nucleic acid analyte from a pathogen having multiple quasispecies. Patient samples include samples of tissue or fluid isolated from an individual or individuals, including but not limited to, for example, skin, plasma, serum, spinal fluid, lymph fluid, synovial fluid, urine, tears, blood cells, organs, tumors, and also to samples of in vitro cell culture constituents (including but not limited to conditioned medium resulting from the growth of cells in cell culture medium, recombinant cells and cell components).

As used herein, the term "amplification" means the process of increasing the relative abundance of one or more specific genes or gene fragments in a reaction mixture with respect to other genes. Numerous amplification methods are available and known to those in the art. Such methods typically utilize the technique of polymerase chain reaction (or PCR) or some other primer extension based methodology. PCR methods are described, for example, in U.S. Pat. Nos. 4,683,194, 4,683,195 and 4,683,202, and 4,800,159 which are incorporated herein by reference. The method is also explained in texts such as Current Protocols in Molecular Biology, (Eds. Ausubel, F. M. et al., (John Wiley & Sons; 1995)), K. Mullis, Cold Spring Harbor Symp. Quant. Biol., 51:263-273 (1986); and C. R. Newton & A. Graham, Introduction to Biotechniques: PCR, 2.sup.nd Ed., Springer-Verlag (New York: 1997), the contents of which are incorporated herein by reference. PCR involves the use of pairs of primers, one for each complementary strand of the duplex DNA (wherein the coding strand is referred to as the "sense strand" and its complementary strand is referred to as the "anti-sense strand), that will hybridize at sites located on either side of a region of interest in a gene. Chain extension polymerization is then carried out in repetitive cycles to increase the number of copies of the region of interest exponentially. To briefly summarize, in the first step of the PCR reaction, the nucleic acid molecules of the sample are transiently heated, and then cooled, in order to denature double stranded molecules. Forward and reverse primers are present in the amplification reaction mixture at an excess concentration relative to the sample target. When the sample is incubated under conditions conducive to hybridization and polymerization, the primers hybridize to the complementary strand of the nucleic acid molecule at a position 3' to the sequence of the region desired to be amplified that is the complement of the sequence whose amplification is desired. Upon hybridization, the 3' ends of the primers are extended by the polymerase. The extension of the primer results in the synthesis of a DNA molecule having the exact sequence of the complement of the desired nucleic acid sample target. The PCR reaction is capable of exponentially amplifying the desired nucleic acid sequences, with a near doubling of the number of molecules having the desired sequence in each cycle. Thus, by permitting cycles of hybridization, polymerization, and denaturation, an exponential increase in the concentration of the desired nucleic acid molecule can be achieved. The amplified polynucleotide may be used as the template for a sequencing reaction. Gelfand et al. have described a thermostable enzyme, "Taq polymerase", derived from the organism *Thermus aquaticus*, which is useful in this amplification process (see U.S. Pat. Nos. 4,889,818; 5,352,600; and 5,079,352 which are incorporated herein by reference). Alternative amplification techniques such as NASBA, 3SR, Qb Replicase, and Branched Chain Amplification are known and available to persons skilled in the art. The term "RT-PCR" refers generally to amplification which includes a reverse transcription step to permit amplification of RNA sequences.

As used herein, the term "sequencing" means the determination of the order of nucleotides in at least a part of a gene. A well known method of sequencing is the "chain termination" method first described by Sanger et al., PNAS (USA) 74(12): 5463-5467 (1977) and detailed in Sequenase® 2.0 product literature (Amersham Life Sciences, Cleveland) and more recently elaborated in European Patent EP-B1-655506, the content of which are all incorporated herein by reference. In this process, DNA to be sequenced is isolated, rendered single stranded, and placed into four vessels. In each vessel are the necessary components to replicate the DNA strand, which include a template-dependent DNA polymerase, a short primer molecule complementary to the initiation site of sequencing of the DNA to be sequenced and deoxyribonucleotide triphosphates for each of the bases A, C, G and T, in a buffer conducive to hybridization between the primer and the DNA to be sequenced and chain extension of the hybridized primer. In addition, each vessel contains a small quantity of one type of dideoxynucleotide triphosphate, e.g. dideoxyadenosine triphosphate ("ddA"), dideoxyguanosine triphosphate ("ddG"), dideoxycytosine triphosphate ("ddC"), dideoxythymidine triphosphate ("ddT"). In each vessel, each piece of the isolated DNA is hybridized with a primer. The primers are then extended, one base at a time to form a new nucleic acid polymer complementary to the template DNA. When a dideoxynucleotide is incorporated into the extending polymer, the polymer is prevented from further extension. Accordingly, in each vessel, a set of extended polymers of specific lengths are formed which are indicative of the positions of the nucleotide corresponding to the dideoxynucleotide in that vessel. These sets of polymers are then evaluated using gel electrophoresis to determine the sequence.

Sequencing of polynucleotides may be performed using either single-stranded or double stranded DNA. Use of polymerase for primer extension requires a single-stranded DNA template. In preferred embodiments, the method of the present invention uses double-stranded DNA in order to obtain confirmatory opposite strand confirmation of sequencing results. Double stranded DNA templates may be sequenced using either alkaline or heat denaturation to separate the two complementary DNA templates into single strands. During polymerization, each molecule of the DNA template is copied once as the complementary primer-extended strand. Use of thermostable DNA polymerases (e.g. Taq, Bst, Tth or Vent DNA polymerase) enables repeated cycling of double-stranded DNA templates in the sequencing reaction through alternate periods of heat denaturation, primer annealing, extension and dideoxy termination. This cycling process effectively amplifies small amounts of input DNA template to generate sufficient template for sequencing.

Sequencing may also be performed directly on PCR amplification reaction products. Although the cloning of amplified DNA is relatively straightforward, direct sequencing of PCR products facilitates and speeds the acquisition of sequence information. As long as the PCR reaction produces a discrete amplified product, it will be amenable to direct sequencing. In contrast to methods where the PCR product is cloned and a single clone is sequenced, the approach in which the sequence of PCR products is analysed directly is generally unaffected by the comparatively high error rate of Taq DNA polymerase. Errors are likely to be stochastically distributed throughout the molecule. Thus, the overwhelming majority of the amplified product will consist of the correct sequence. Direct sequencing of PCR products has the advantage over sequencing cloned PCR products in that (1) it is readily standardized because it is simple enzymatic process that does not depend on the use of living cells, and (2) only a single sequence needs to be determined for each sample.

As used herein, the terms "nucleic acid," "polynucleotide," and "oligonucleotide" refer to primers, probes, oligomer fragments to be detected, oligomer controls and unlabeled blocking oligomers and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases. There is no intended distinction in length between the term "nucleic acid", "polynucleotide" and "oligonucleotide", and these terms are considered to be equivalent and interchangeable, unless expressly indicated otherwise. These terms refer only to the primary structure of the molecule. Thus, these terms include double- and single-stranded DNA, as well as double- and single-stranded RNA. The oligonucleotide is comprised of a sequence of approximately at least 6 nucleotides, preferably at least about 10-12 nucleotides, and more preferably at least about 15-25 nucleotides corresponding to a region of the designated nucleotide sequence. Nucleic acids may also substitute standard nucleotide bases with nucleotide isoform analogs, including, but not limited to iso-C and iso-G bases, which may hybridize more or less permissibly than standard bases, and which will preferentially hybridize with complementary isoform analog bases. Many such isoform bases are described, for example, at www.idtdna.com. The term "corresponding to," as used herein, as used herein to define a nucleic acid sequence in terms of a reference nucleotide sequence, means nucleotide sequences that match all or part of the reference sequence, and nucleotide sequences that are the complement of all or part of the reference sequence.

Oligonucleotides are not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature; and (3) is not found in nature.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

The term "HR1," as used herein refers to the heptad repeat 1 (HR1) region of the gp41 subunit of the HIV-1 env protein, represented by nucleotides 7388-7549 of SEQ ID NO:1.

The term "consisting essentially of," as used herein in reference to specified nucleotide sequences, means the specified sequences and any additional sequence that does not contain the predetermined length polymorphisms. For example, the region consisting essentially of the HR1 domain of HIV-1 env gp41 region, includes all or a part of HR1 (nucleotides 7388-7549 of SEQ ID NO:1) and any additional nucleotide sequence of the adjacent 5' and 3' regions that do not include length polymorphisms located outside the HR1 domain that may occur on a sufficiently frequent basis among the population of prospective patients to adversely affect the reliability of sequence results. Such length polymorphisms may be located, for example, within approximately the first 25 or last 60 nucleotides of the gp41 domain. As used herein, a region consisting essentially of the HR1 domain will preferably correspond to the region of nucleotides 7329-7614 of SEQ ID NO:1, or fragments thereof of 15 or more nucleotides. More preferably, the region consisting essentially of the HR1 domain will correspond to the region of nucleotides 7388-7549 of SEQ ID NO:1 or fragments thereof of 15 or more nucleotides. The region consisting essentially of the HR1 domain may also correspond to the region of nucleotides 7492-7522 of SEQ ID NO:1 or fragments thereof of 15 or more nucleotides. It is understood that because the term "consisting essentially of" is used to define specified sequences that exclude predetermined length polymorphisms, the present invention may include sequences that encompass other length polymorphisms, whether known or unknown. The utility of the present invention arises primarily in situations where length polymorphisms give rise to a new quasispecies of a pathogenic vector, and that quasispecies occurs within the patient population with sufficient frequency that the clinical failure rate is unacceptably high. Thus, the present invention contemplates that the region containing the mutation of interest that is sequenced, while "exclusive of the predetermined length polymorphisms," may still include other length polymorphisms that, for example, are either unknown or that do not occur within the patient population with sufficient frequency that the clinical failure rate has been determined to be unacceptably high. It is sufficient, for purposes of the present invention, that even a single predetermined length polymorphisms has been excluded from the region sequenced in order to enable complementary strand confirmation of sequences from quasispecies of the vector defined by that predetermined length polymorphisms.

The term "encompass," as used herein in reference to the location of a primer relative to a reference location, means that a PCR extension primer is located so as to generate primer extension products that include specified nucleotides or regions of nucleotides. The primer may include nucleotide sequences that correspond to or are complementary to all or part of the reference location. Alternatively, the primer may be complementary to a region located 3' of the reference location.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature.

The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primer and use of the method. For example, depending on the complexity of the target sequence, the oligonucleotide primer typically contains 10-50, and preferably 15-25 nucleotides, although it may contain more or fewer nucleotides. Short primer molecules generally require lower temperatures to form sufficiently stable hybrid complexes with the template.

The term "extension primer," as used herein, means a polynucleotide sequence that is complementary to a template sequence, and which is capable of hybridizing to and extending a sequence under polymerase chain reaction conditions to produce a primer extension product.

The term "complement," and its related adjective form "complementary," when used in reference to two nucleic acid sequences, means that when two nucleic acid sequences are aligned in anti-parallel association (with the 5' end of one sequence paired with the 3' end of the other sequence) the corresponding G and C nucleotide bases of the sequences are paired, and the corresponding A and T nucleotide bases are paired. Certain bases not commonly found in natural nucleic acids may be included in the nucleic acids of the present invention and include, for example, inosine and 7-deazaguanine.

The term "allele," used herein, means a specific version of a nucleotide sequence at a polymorphic genetic locus.

The term "polymorphic site," as used herein means a given nucleotide location in a genetic locus which is variable within a population.

The term "genetic locus," as used herein means a specific position or location of a nucleotide or region of nucleotides in a DNA sequence or in the corresponding RNA strand packaged in a viral particle, which is derived from the transcribed DNA sequence.

The nucleotides adenosine, cytosine, guanine and thymine are represented by their one-letter codes A, C, G, and T respectively. In representations of degenerate primers, the symbol R refers to either G or A, the symbol Y refers to either T/U or C, the symbol M refers to either A or C, the symbol K refers to either G or T/U, the symbol S refers to G or C, the symbol W refers to either A or T/U, the symbol B refers to "not A", the symbol D refers to "not C", the symbol H refers to "not G", the symbol V refers to "not T/U" and the symbol N refers to any nucleotide. In the specification and claims of this application, a degenerate primer refers to any or all of the combinations of base choices and to either DNA or the corresponding RNA sequence (i.e., with T replaced by U). Thus, a degenerate primer may represent a single species, or a mixture of two species which fall within the choices, or a mixture of three choices which fall with the choices, and so on up to a mixture containing all the possible combinations. Isoform nucleotide bases are represented using nomenclature generally accepted by those in the art.

The term "oligonucleotide primer," as used herein, means a molecule comprised of more than three deoxyribonucleotides or ribonucleotides. Its exact length will depend on many factors relating to the ultimate function and use of the oligonucleotide primer, including temperature of the annealing reaction, and the source and composition of the primer. Amplification primers must be sufficiently long to prime the synthesis of extension products in the presence of the agent for polymerization. The oligonucleotide primer is capable of acting as an initiation point for synthesis when placed under conditions which induce synthesis of a primer extension product complementary to a nucleic acid strand. The conditions can include the presence of nucleotides and an inducing agent such as a DNA polymerase at a suitable temperature and pH. In preferred embodiments, the primer is a single-stranded oligodeoxyribonucleotide of sufficient length to prime the synthesis of an extension product from a specific sequence in the presence of an inducing agent. In one aspect of the present invention, the oligonucleotide primers are from about 10 to about 50 nucleotides long, and preferably from about 15 to about 30 nucleotides long, although a primer may contain more or fewer nucleotides. The oligonucleotide primers are generally at least 15, 16, 17, 18, 19, 20, 21, 22, 23, 24, or 25 nucleotides long. More preferably, primers will contain around 20-25 nucleotides. Sensitivity and specificity of the oligonucleotide primers are determined by the primer length and uniqueness of sequence within a given sample of template nucleic acid. Primers which are too short, for example, may show non-specific binding to a wide variety of sequences.

The oligonucleotide primers used in the present invention may also include universal primers. Universal primers are used for convenience in amplifying and sequencing a polynucleotide sequence that has been inserted into a standard vector that contains sequences complementary to the universal primers. Universal sequencing primers are well-known to those in the art, and include, for example, primers referred to as T7, SP6, M13(−40), M13(−20), and M13/pUC. An amplification primer may be designed so as to include the complement of a universal primer, so that the amplification product (the amplicon) incorporates a universal primer site, thereby facilitating subsequent sequencing using complementary universal sequencing primers.

The primers of the present invention may also include random additional sequence between the primer sequence and the sequence of interest to facilitate more accurate sequencing. Because the initial 10-50 base pairs of a sequence are typically unreadable, the addition of a 10-50 base pair random sequence shifts the critical sequence downstream of the initial unreadable sequence so that the sequence of interest is located within the region where accurate reading of the sequence occurs.

The term "reverse transcription" means the process of generating a DNA complement to an RNA molecule, and is generally accomplished with the use of a reverse transcriptase enzyme. A primer may be used to initiate polymerization; this primer may be one of a primer pair later used for PCR amplification. The RNA molecule is then separated from the copied DNA ("cDNA") or degraded by an RNAse H activity of an enzyme thus allowing the second strand of cDNA to be generated by a template dependent DNA polymerase. This method is disclosed in Units 3.7 and 15.4 of Current Protocols in Molecular Biology, Eds. Ausubel, F. M. et al, (John Wiley & Sons; 1995), the contents of which are incorporated herein by reference.

The practice of the present invention will employ, unless otherwise indicated, conventional techniques of molecular biology, microbiology, recombinant DNA techniques, oligonucleotide synthesis which are within the skill of the art. Such techniques are explained fully in the literature. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)); Oligonucleotide Synthesis (M. J. Gait, ed., 1984); Nucleic Acid Hybridization (B. D. Hames & S. J. Higgins, eds., 1984); A Practical Guide to Molecular Cloning (B. Perbal, 1984); and a series, Methods in Enzymology (Academic Press, Inc.), the contents of all of which are incorporated herein by reference.

Methods of the Invention

The present invention is directed to a method for detecting the presence or absence of a mutation of interest that is adjacent to a different predetermined length polymorphism. The methods and reagents of the present invention are most advantageously used for obtaining polynucleotide sequence of an exogenous vector, such as an infectious pathogen, in a patient sample that may contain multiple quasispecies of the vector relative to the length polymorphism. The presence of mixed length polymorphisms among quasispecies in a single patient sample precludes confirmation of the sequence results from the complementary opposite strand DNA of the vector where the region that is sequenced encompasses the length polymorphism. Generally, the method of the present invention comprises selectively sequencing both complementary strands of the region associated with the mutation of interest, exclusive of the adjacent predetermined length polymorphism, and comparing the sequence of the complementary strands to confirm that the sequence of each strand is the complement of the other strand at all nucleotide bases.

While the methods of the present invention were developed initially with respect to the HIV-1 gene, such methods are nevertheless applicable to any pathogen having length polymorphisms among multiple quasispecies. Accordingly, the present invention is directed to a method for detecting the presence or absence of a mutation of interest in the nucleic acid of a pathogen, such as HIV-1, wherein the mutation of interest is located adjacent to a length polymorphism defining multiple quasispecies of the pathogen, comprising:
   a) obtaining from the patient sample a double-stranded DNA template encompassing the mutation of interest;
   b) sequencing a first strand of a region of the DNA template containing the mutation of interest, exclusive of the length polymorphism;
   c) sequencing a second strand of a region of the DNA template containing the mutation of interest, exclusive of the length polymorphism; and
   d) comparing the sequence of the first strand with the sequence of the second strand to obtain complementary strand confirmation of the sequence of the mutation of interest. Sequencing in steps (b) and (c) may be performed using any suitable DNA template capable of yielding genetic sequence information of the specified region of the exogenous vector.

In another aspect, the present invention is directed to a method for detecting the presence or absence of a mutation of interest in the nucleic acid of a pathogen, such as HIV-1, wherein the mutation of interest is located adjacent to a length polymorphism defining multiple quasispecies of the pathogen, comprising:
   a) obtaining from the patient sample a double-stranded DNA template encompassing the mutation of interest;
   b) amplifying a first region of the DNA template containing both the mutation of interest and the length polymorphism;
   c) sequencing a first strand of a region of the DNA template containing the mutation of interest, exclusive of the length polymorphism;
   d) sequencing a second strand of a region of the DNA template containing the mutation of interest, exclusive of the length polymorphism; and
   e) comparing the sequence of the first strand with the sequence of the second strand to obtain complementary strand confirmation of the sequence of the mutation of interest.

In this method, the amplification step includes the mutation of interest and the length polymorphism, and it is in the sequencing steps (c) and (d) that the length polymorphism is excluded.

In yet another aspect, the present invention is directed to a method for detecting the presence or absence of a mutation of interest in the nucleic acid of a pathogen, such as HIV-1, wherein the mutation of interest is located adjacent to a length polymorphism defining multiple quasispecies of the pathogen, comprising:
   a) obtaining from the patient sample a double-stranded DNA template encompassing the mutation of interest;
   b) amplifying a first genetic region of the DNA template comprising the mutation of interest, exclusive of the length polymorphism;
   c) sequencing a first strand of a region of the DNA template containing the mutation of interest, exclusive of the length polymorphism;
   d) sequencing a second strand of a region of the DNA template containing the mutation of interest, exclusive of the length polymorphism; and
   e) comparing the sequence of the first strand with the sequence of the second strand to obtain complementary strand confirmation of the sequence of the mutation of interest.

In this embodiment, it is in the amplification step that the length polymorphism is excluded, and subsequent sequencing of the amplified region or a portion of the amplified region also excludes the length polymorphism.

In a one aspect of the invention, the mutation of interest is located in a region of HIV selected from the group consisting of: gp41 and gp120. In another aspect of the invention, the mutation of interest is located in the HIV-1 envelope glycoprotein gp41. In yet another aspect of the invention, the mutation of interest is located within positions 36-45 gp41.

As illustrated by the above embodiments, the common feature of the various embodiments of the present invention is the exclusion of the length polymorphism within the region of the DNA that is sequenced, permitting subsequent comparison of the first strand sequence with the second strand sequence to obtain complementary strand confirmation of the sequence of the mutation of interest, without confounding results as a consequence of having multiple length polymorphism quasispecies present having different nucleic acid lengths. It will be understood by those in the art that various approaches may be utilized prior to the sequencing step to provide a DNA template that can yield sequence data exclusive of the length polymorphism.

Source of DNA

In one aspect of the invention, the method comprises first obtaining from the patient sample a double-stranded polynucleotide template encompassing the mutation of interest. The double-stranded polynucleotide template may initially comprise genomic DNA or a fragment of genomic DNA. This template will encompass not only the mutation of interest, but may also encompass the region containing the length polymorphism giving rise to multiple quasispecies.

A double-stranded polynucleotide template will typically be prepared from a patient sample by treating a patient sample containing DNA so as to make all or a portion of the DNA in the sample accessible for hybridization with oligonucleotide primers, for example by lysis, centrifugation to remove cellular debris and proteolytic digestion to expose the DNA. The DNA template may therefore contain only nuclear DNA, only mitochondrial DNA, or some sub-fraction of nuclear or mitochondrial DNA obtained by isolation from a tissue sample. The DNA template may also be prepared by conversion, for example by reverse transcription, of a total mRNA preparation or the genome of an RNA virus to cDNA; DNA isolated from an individual bacterial colony growing on a plate or from an enriched bacterial culture; and a viral DNA preparation where substantially the entire viral genome is isolated.

DNA can be prepared from fluid samples, e.g., blood or urine or tissue samples by any of a number of techniques, including lysis, centrifugation to remove cellular debris and proteolytic digestion to expose the DNA; salt precipitation or standard SDS-proteinase K-phenol extraction. Samples can also be prepared using kits, for example the Pure Gene DNA Isolation Kit (Gentra).

Amplification of Nucleic Acids

Preferred embodiments of the present invention include the step of amplifying DNA to provide an abundant source of DNA for subsequent sequencing. In one aspect, the method of the present invention optionally comprises amplifying a first region of the DNA template containing both the mutation of interest and the length polymorphism. An amplification product that contains the predetermined length polymorphism will subsequently be sequenced using primers that exclude the length polymorphism.

Alternatively, in another aspect, the method may comprise selectively amplifying a first genetic region of the DNA template containing the region containing the mutation of interest, exclusive of the length polymorphism. An amplification product that excludes the predetermined length polymorphism may be sequenced directly, using the same primers corresponding to the amplification primers, using primers complementary to a different region of the amplified fragment, or using universal primers complementary to a universal primer template incorporated into the amplification product during PCR (using primers that include the universal primer).

Typically, prior to sequencing, a sequencing template is prepared by first amplifying a region of DNA that encompasses the target region to be sequenced. It is not necessary that the sequence to be amplified be present initially in a pure form; it may be a minor fraction of a complex mixture or a portion of nucleic acid sequence. The starting nucleic acid may contain more than one desired specific nucleic acid sequence which may be the same or different. Therefore, the present process is useful not only for producing large amounts of one specific nucleic acid sequence, but also for amplifying simultaneously more than one different specific nucleic acid sequence located on the same or different nucleic acid molecules if more than one of the base pair variations in sequence is present.

In one aspect, the present invention is directed to amplification and sequencing primers used in a method for genotyping HIV-1 env. The method utilizes well-known methods for amplifying specific nucleic acid sequences using the technique of polymerase chain reaction (or PCR) or some other primer extension based methodology. Polymerase chain reaction (PCR) is very widely known in the art. For example, U.S. Pat. Nos. 4,683,195, 4,683,202, and 4,800,159; K. Mullis, Cold Spring Harbor Symp. Quant. Biol., 51:263-273 (1986); and C. R. Newton & A. Graham, Introduction to Biotechniques: PCR, 2.sup.nd Ed., Springer-Verlag (New York: 1997), the disclosures of which are incorporated herein by reference, describe processes to amplify a nucleic acid sample target using PCR amplification extension primers which hybridize with the sample target. As the PCR amplification primers are extended, using a DNA polymerase (preferably thermostable), more sample target is made so that more primers can be used to repeat the process, thus amplifying the sample target sequence. Typically, the reaction conditions are cycled between those conducive to hybridization and nucleic acid polymerization, and those that result in the denaturation of duplex molecules.

To briefly summarize, in the first step of the reaction, the nucleic acid molecules of the sample are transiently heated, and then cooled, in order to denature double stranded molecules. Forward and reverse primers are present in the amplification reaction mixture at an excess concentration relative to the sample target. When the sample is incubated under conditions conducive to hybridization and polymerization, the primers hybridize to the complementary strand of the nucleic acid molecule at a position 3' to the sequence of the region desired to be amplified that is the complement of the sequence whose amplification is desired. Upon hybridization, the 3' ends of the primers are extended by the polymerase. The extension of the primer results in the synthesis of a DNA molecule having the exact sequence of the complement of the desired nucleic acid sample target. The PCR reaction is capable of exponentially amplifying the desired nucleic acid sequences, with a near doubling of the number of molecules having the desired sequence in each cycle. Thus, by permitting cycles of hybridization, polymerization, and denaturation, an exponential increase in the concentration of the desired nucleic acid molecule can be achieved.

Preparation of Nucleic Acid Amplification Templates

The present invention is directed to methods of amplifying and sequencing pathogens, including HIV-1 env and its variant forms. The method of the present invention may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid.

It is not necessary that the sequence to be amplified be present initially in a pure form; it may be a minor fraction of a complex mixture or a portion of nucleic acid sequence. The starting nucleic acid may contain more than one desired specific nucleic acid sequence which may be the same or different. Therefore, the present process is useful not only for producing large amounts of one specific nucleic acid sequence, but also for amplifying simultaneously more than one different specific nucleic acid sequence located on the same or different nucleic acid molecules if more than one of the base pair variations in sequence is present.

The nucleic acid templates may be obtained from any source, for example, from plasmids such as pBR322, from cloned DNA or RNA, or from natural DNA or RNA from any source, such as HIV infected plasma or serum obtained from patients. DNA or RNA may be extracted from blood, tissue material or amniotic cells by a variety of techniques such as that described by Maniatis et al., Molecular Cloning (1982), 280-281.

The cells may be directly used without purification of the nucleic acid if they are suspended in hypotonic buffer and heated to about 90°-100° C., until cell lysis and dispersion of intracellular components occur, generally about 1 to 15 minutes. After the heating step the amplification reagents may be added directly to the lysed cells. This direct cell detection method may be used on peripheral blood lymphocytes and amniocytes.

The target nucleic acid contained in the sample will initially be in the form of RNA, and is preferably reverse transcribed into cDNA, and then denatured, using any suitable denaturing method, including physical, chemical, or enzymatic means, which are known to those of skill in the art. A preferred physical means for strand separation involves heating the nucleic acid until it is completely (>99%) denatured. Typical heat denaturation involves temperatures ranging from about 80° C. to about 105° C., for times ranging from a few seconds to minutes. As an alternative to denaturation, the target nucleic acid may exist in a single-stranded form in the sample, such as, for example, single-stranded RNA or DNA viruses.

The denatured nucleic acid strands are then incubated with preselected oligonucleotide primers, and, optionally, a labeled oligonucleotide (referred to herein as a "probe") for purposes of detecting the amplified sequence) under conditions that facilitate the binding of the primers and probes to the single nucleic acid strands. As known in the art, the primers are selected so that their relative positions along a duplex sequence are such that an extension product synthesized from one primer, when the extension product is separated from its template (complement), serves as a template for the extension of the other primer to yield a replicate chain of defined length.

Sequencing of Nucleic Acids

Amplification of DNA as described above will result in an abundant source of DNA for sequencing. The polynucleotide templates prepared as described above are sequenced using any of the numerous methods available and known to those in the art for sequencing nucleotides.

In preferred aspects of the present invention, the DNA template used for sequencing will be double stranded. Double stranded DNA permits simultaneous sequencing of complementary strands, enabling confirmation of correct sequence results by comparison of the sequence obtained from each strand, which should be exactly complementary.

The amplification methods used in the present invention may also be simultaneously used in conjunction with sequencing. Methods for simultaneous amplification and sequencing are widely known in the art, and include coupled amplification and sequence (CAS) (described by Ruano and Kidd, Proc. Nat'l. Acad. Sci. (USA) 88(7): 2815-2819 (1991), and in U.S. Pat. No. 5,427,911, which are incorporated herein by reference), and CLIP amplification and sequencing (described in U.S. Pat. No. 6,007,983, and in J. Clin. Microbiology 41(4); 1586-1593 (April 2003) which are incorporated herein by reference). CLIP sequencing subjects PCR amplification fragments previously generated to simultaneous PCR amplification and direct sequencing. In CAS sequencing, a sample is treated in a first reaction stage with two primers and amplified for a number of cycles to achieve 10,000 to 100,000-fold amplification. A ddNTP is then added during the exponential phase of the amplification reaction, and the reaction is processed for additional thermal cycles to produce chain-terminated sequencing fragments. The CAS process requires an intermediate addition of reagents (the ddNTP reagents), which introduces opportunity for error or contamination and increases the complexity of any apparatus which would be used for automation. The CAS methodology is therefore preferably combined with CLIP sequencing, which subjects PCR amplification fragments previously generated to simultaneous PCR amplification and direct sequencing. Simultaneous amplification and sequencing using the CLIP® method may be accomplished, for example, using the reagents and conditions described and provided in commercially available kits, such as the TRUGENE® HIV genotyping kit (Bayer HealthCare LLC).

In particular aspects, the present invention relates to sequencing of infectious pathogens, such as bacteria or viruses, such as Hepatitis B, Hepatitis C, and Human Immunodeficiency Virus, in particular HIV-1 env, and their variant forms. The double stranded DNA template used in the method of the present invention may be derived from, for example, DNA or RNA, including messenger RNA, which may be single stranded or double stranded. In addition, the DNA template may be in the form of a DNA-RNA hybrid which contains one strand of DNA and one strand of RNA. A mixture of any of these nucleic acids may also be employed, or the nucleic acids produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid.

Sequencing the HR1 and/or HR2 Domains of HIV-1 gp41

The present invention includes a novel method and reagents for genotyping the HIV-1 transmembrane glycoprotein (gp41) in a sample suspected of containing the HIV-1 virus.

The present invention addresses the above-mentioned problem, by providing primers that encompass all or part of the HR1 and HR2 domains of gp41, or all or part of the HR1 domain of gp41.

The sequencing primers of the present invention consist of oligonucleotides specific to HIV-1, which can be used to amplify and sequence a portion of gp41 DNA. In accordance with methods known to those in the art, a sample obtained from an individual suspected of being infected with the HIV-1 virus is used to recover viral RNA, either in the form of RNA or DNA. Viral HIV-1 RNA obtained from the sample is reverse transcribed to cDNA. The cDNA template is then amplified, using Polymerase Chain Reaction or some other primer extension based method. The resulting amplified fragment is then initially sequenced with a set of primers encompassing the gp41 subunit, encompassing the HR1 and HR2 domains, or alternatively encompassing the HR1 domain, using cycle sequencing methods or CLIP™ bi-directional sequencing.

One particular aspect of the present invention is a method for amplifying and genotyping the gp41 subunit of the HIV-1 env gene in a sample suspected of containing the HIV-1 virus, comprising (1) amplifying the HIV-1 env region, (2) determining sequence of a region encompassing both the HR1 and HR2 domains of gp41.

The present invention is generally directed to a novel method and reagents for sequencing and genotyping the HR1 domain of the HIV-1 transmembrane glycoprotein (gp41) in a sample suspected of containing the HIV-1 virus. The higher complexity of the gp41 region surrounding the first heptad repeat domain (HR1) was found to be due to relatively frequent occurrence of insertion or deletion mutations near the HR1 domain. Mutations in the HR1 domain are known to occur, for example, at positions 36 to 38 of the HIV-1 envelope glycoprotein gp41. Particular mutations include G36V/D/S, I37V, V38A/M/E, Q39R, Q40H, N42T, N43H/E/D/S, L44M, L45M. Mixtures of HIV-1 viral populations with length polymorphisms were found to occur in plasma, resulting in inconsistent HR1 nucleotide sequence data and conflicting bi-directional sequence data. This problem was not previously recognized, possibly because the methods have relied upon cloning of RT-PCR products before sequencing or because uni-directional data has been accepted without confirmatory bi-directional data. The present invention addresses the above-mentioned problem, by providing a method and primers for sequencing a region consisting essentially of the HR1 domain of HIV-1 env, but excluding the regions of higher variability responsible for length polymorphisms. The primers of the present invention are therefore useful for confirming sequence for samples that cannot be accurately characterized using sequencing primers that attempt to sequence through the region containing length polymorphisms before reaching the HR1 domain.

Sequencing Primers for gp41

The sequencing primers of the present invention include both forward primers and reverse primers, which may be labeled with a detectable label. For most common sequencing instruments, a fluorescent label is desirable, although other labels types including colored, chromogenic, fluorogenic (including chemiluminescent) and radiolabels could also be employed. The primer combination may include other reagents appropriate for reverse transcription, amplification or sequencing, and may, of course, include HIV-1 genetic material for analysis.

In one aspect, the present invention includes a method and primers for determining the sequence of the HR1 and HR2 domains of gp41. In a particular embodiment, present invention includes a method and primers for determining the sequence of both DNA strands (bi-directional) of the region encompassing the HR1 and HR2 domains of gp41.

In another aspect, the present invention also includes methods and primers for sequencing a region consisting essentially of the HR1 domain of the HIV-1 glycoprotein gp41. The sequencing primers of the present invention may be any suitable sequencing primer having the desired specificity to sequence a region consisting essentially of the HR1 domain of HIV-1. In accordance with methods known to those in the art, a sample obtained from an individual known to be or suspected of being infected with the HIV-1 virus is used to recover viral RNA, either in the form of RNA or DNA. Viral HIV-1 RNA obtained from the sample is reverse transcribed to cDNA. The cDNA template is then amplified, using Polymerase Chain Reaction or some other primer extension based method. In preferred embodiments, the amplified region encompasses the region encoding the HIV-1 env protein, although broader or narrower regions are also suitable for use as a template for sequencing specific regions of the HIV env domain. The resulting amplified fragment is then sequenced (for example, by cycle sequencing or CLIP® bi-directional sequencing) with a set of primers or, in the case of uni-directional sequencing, a single primer, that provides sequence for a region consisting essentially of the HR1 domain, but which does not sequence through regions of length polymorphisms caused by insertion and/or deletion mutations near the HR1 domain prior to sequencing the HR1 region itself. The primers of the present invention are thus complementary to regions situated between the regions of length polymorphisms caused by insertion and/or deletion mutations and the HR1 domain itself, so that extension of the primer proceeds in the direction away from the length polymorphisms towards the HR1 domain. In a particular embodiment, the present invention provides a method for sequencing the HR1 domain of the gp41 subunit of the HIV-1 env gene in a sample suspected of containing the HIV-1 virus, comprising determining the nucleotide sequence of a region consisting essentially of the HR1 domain of gp41, but excluding regions adjacent to the HR1 domain that include mutations associated with length polymorphisms.

The primers of the present invention enable determination of the sequence of HR1 in clinical settings where other primers result in sequence data that is difficult to interpret as a result of length polymorphisms among mixed plasma subpopulations of HIV-1. These primers may be utilized to provide confirmation of HR1 mutations, but may also be used as an alternative sequencing primer set for HR1 only coverage.

The primers of the present invention may be a single primer for use in determining the sequence of a single strand of DNA. Alternatively, in a preferred embodiment of the invention, the primers are a combination of primers for determining the sequence of both DNA strands (bi-directional sequence) of the region encompassing the HR1 domain of gp41. The sequencing primers of the present invention may therefore include forward primers, reverse primers, or both forward and reverse primers. When used for clinical purposes in determining the genotype of HIV-1 from a patient sample, it is desirable to obtain sequence of both forward and reverse strands of DNA, thereby obtaining confirmation of sequence results. It is understood, however, that the sequencing primers of the present invention may be used when only obtaining sequence of one or the other of the forward and reverse strands.

The primers of the present invention are specific to regions between drug resistance associated mutations within HR1 and length polymorphisms found among mixed plasma subpopulations of HIV. In functional terms, such primers can be defined as primers that are capable of generating sequencing reaction products that do not include insertion or deletion mutations associated with length polymorphisms found among mixed plasma subpopulations of HIV. Because the objective is to obtain consistent sequence data for the HR1 region (specifically, the drug resistance mutations located within HR1), it is contemplated that primers will initiate extension in the direction that first provides sequence data for the HR1 region (away from length polymorphisms located in the opposite direction of extension), followed by sequence that may include length polymorphisms on the other side of HR1. By first generating sequence through the HR1 region (prior to generating sequence through the region of length polymorphisms), consistent nucleotide sequence data for the HR1 region is generated. The existence of confounded sequence resulting from the length polymorphisms following the HR1 region does not therefore adversely affect the sequence results of the HR1 region itself. It is therefore understood that the primers may sequence through a region of length polymorphism, provide such sequence is generated after the sequence for HR1 has been generated first.

Examples of acceptable sequencing primers are disclosed below. Although the sequencing primers of the present invention are preferably selected from among primers having the same sequence as disclosed below, it is contemplated that the present invention includes degenerate sequences having specificity for major HIV-1 subtypes, but which may also have specificity for less common sub-types. The design and construction of such degenerate sequences is well know to those in the art.

Generally, DNA sequencing primers consist of 15 or more nucleotide bases, preferably from 18 to 30 nucleotide bases. The sequencing primers may also include fragments of the above primers having 18, 19, 20, 21, 22, 23, 24, or 25 nucleotides. Preferably, primers have a melting temperature (Tm) in the range of 52 C to 65 C, particularly if templates are GC rich, since this can lead to secondary priming artifacts and noisy sequences. In addition, preferred primers will not dimerize or form significant hairpins, and will lack secondary priming sites. Also, primers will have low specific binding at the 3' end (i.e., will have a lower GC content, preferably from 40-60%, to avoid mispriming. Computer software is available to design primers with these characteristics, which includes LaserGene (DNAStar), Oligo (National Biosciences, Inc.), MacVector (Kodak/IBI) and the GCG suite. In addition, primers may be designed to satisfy the above criteria using the Whitehead Institute PCR primer program, available at genome.wi.mit.edu/cgi-bin/primer/primer3.cgi. Additional design criteria is known and available to those skilled in the art.

Because sequencing primers, as opposed to amplification primers, may not be mixed together if they do not have the same location for the 3' base, specific degenerate base positions are illustrated below, although it is to be understood that the 3' and 5' locations may be modified. The 5' nucleotide location may be changed to include regions of greater sequence conservation or to modify melting temperature and stringency of binding. A non-degenerate primer set is preferred, provided the success rate is sufficient to obtain sequence for the desired HIV-1 subtypes. Reaction conditions may also be adjusted to optimize performance. Examples of potential modifications of sequencing primers are disclosed below.

In a particular embodiment, the region encompassing both the HR1 and HR2 domains of gp41 is sequenced using sequencing primers selected from the following:

```
SEQ ID NO: 2     5'-GCACCXACSARGGCAAAGAGAMGAGYGG-3'

SEQ ID NO: 3         5'-ACCAAGGCAAAGAGAAGAGTGG-3'

SEQ ID NO: 4        5'-CCCACCAAGGCAAAGAGAAGAGTGG-3'

SEQ ID NO: 5     5'-GCACCCACCAAGGCAAAGAGAAGAGTGG-3'

SEQ ID NO: 6     5'-GCACCCACCAAGGCAAAGAGAAGAGYGG-3'

SEQ ID NO: 7     5'-GCACCCACCAAGGCAAAGAGAMGAGYGG-3'

SEQ ID NO: 8     5'-GCACCCACCAGGGCAAAGAGAMGAGYGG-3'

SEQ ID NO: 9     5'-GCACCCACGAGGGCAAAGAGAMGAGYGG-3'

SEQ ID NO: 10    5'-GCACCNACGAGGGCAAAGAGAMGAGYGG-3'

SEQ ID NO: 11         5'-ACGAGGGCAAAGAGAMGAGYGG-3'

SEQ ID NO: 12          5'-CCAAGGCAAAGAGAAGAGTG-3'

SEQ ID NO: 13            5'-CGAGGGCAAAGAGAMGAGYG-3'

SEQ ID NO: 14    5'-GCACCCACCAAGGCAAAGAGAAGAGTGG-3'

SEQ ID NO: 15         5'-ACCAAGGCAAAGAGAAGAGTGG-3'
```

```
                    -continued
SEQ ID NO: 16    5'-tartaggaggnttrataggnttaagaata-3'

SEQ ID NO: 17          3'-gtaggaggcttgataggtttaag-5'

SEQ ID NO: 18         3'-tagtaggaggcttgataggtttaag-5'

SEQ ID NO: 19    3'-tartaggaggcttgataggtttaag-5'

SEQ ID NO: 20    3'-tartaggaggnttgataggtttaag-5'

SEQ ID NO: 21    3'-tartaggaggnttrataggtttaag-5'

SEQ ID NO: 22    3'-tartaggaggnttrataggnttaag-5,

SEQ ID NO: 23    3'-tartaggaggnttrataggnttaagaata-5'

SEQ ID NO: 24          3'-ggaggnttrataggnttaagaata-5'

SEQ ID NO: 25          3'-ggvggnttrataggnttaagaata-5'

SEQ ID NO: 26            3'-taggaggnttrataggnttaag-5'

SEQ ID NO: 27            3'-ggaggcttggtaggtttaaga-5'

SEQ ID NO: 28            3'-ggvggnttrataggnttaaga-5'

SEQ ID NO: 29    3'-tagtaggaggcttgataggtttaagaata-5'

SEQ ID NO: 30       3'-gtaggaggcttgataggtttaag-5'
```

The sequencing primers may include, for example, at least one forward sequencing primer selected from the group consisting of the following:

```
SEQ ID NO: 2     5'-GCACCXACSARGGCAAAGAGAMGAGYGG-3'

SEQ ID NO: 3         5'-ACCAAGGCAAAGAGAAGAGTGG-3'

SEQ ID NO: 4        5'-CCCACCAAGGCAAAGAGAAGAGTGG-3'

SEQ ID NO: 5     5'-GCACCCACCAAGGCAAAGAGAAGAGTGG-3'

SEQ ID NO: 6     5'-GCACCCACCAAGGCAAAGAGAAGAGYGG-3'

SEQ ID NO: 7     5'-GCACCCACCAAGGCAAAGAGAMGAGYGG-3'

SEQ ID NO: 8     5'-GCACCCACCAGGGCAAAGAGAMGAGYGG-3'

SEQ ID NO: 9     5'-GCACCCACGAGGGCAAAGAGAMGAGYGG-3'

SEQ ID NO: 10    5'-GCACCNACGAGGGCAAAGAGAMGAGYGG-3'

SEQ ID NO: 11         5'-ACGAGGGCAAAGAGAMGAGYGG-3'

SEQ ID NO: 12          5'-CCAAGGCAAAGAGAAGAGTG-3'

SEQ ID NO: 13            5'-CGAGGGCAAAGAGAMGAGYG-3'

SEQ ID NO: 14    5'-GCACCCACCAAGGCAAAGAGAAGAGTGG-3'
```

In one embodiment of the present invention, the set of bi-directional primary sequencing primers includes a first primer comprising the nucleotide sequence of SEQ ID NO:2, and fragments thereof of 15 or more nucleotides, inclusive of the 3' terminus. SEQ ID NO:2 describes a set of degenerate primers that may be used as the forward primer, where X is 5-nitroindole or C, S represents G or C, R represents G or A, M represents A or C, and Y represents T or C. Primers degenerate at Y(T/C) are designed to detect rare isolates of both the B and A HIV subtypes. Similarly, primers degenerate at M(A/C) are designed to detect F-type HIV recombinants. Other variations of the above sequences may be utilized to permit detection of other HIV variants.

In another embodiment, the present invention includes a set of bi-directional primary sequencing primers that includes a first primer selected from the group consisting of SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, and SEQ ID NO:13, and fragments thereof of 15 or more nucleotides.

In yet another embodiment, the present invention includes a set of bi-directional primary sequencing primers that includes a first primer comprising the sequence of SEQ ID NO:14, and fragments thereof of 15 or more nucleotides.

In yet another embodiment, the present invention includes a set of bi-directional primary sequencing primers includes a first primer comprising the sequence of SEQ ID NO:3.

The primary sequencing primers may also include at least one reverse sequencing primer selected from the group consisting of the following:

```
SEQ ID NO: 15   5'-ACCAAGGCAAAGAGAAGAGTGG-3'
SEQ ID NO: 16   5'-tartaggaggnttrataggnttaagaata-3'
SEQ ID NO: 17      3'-gtaggaggcttgataggtttaag-5'
SEQ ID NO: 18      3'-tagtaggaggcttgataggtttaag-5'
SEQ ID NO: 19      3'-tartaggaggcttgataggtttaag-5'
SEQ ID NO: 20      3'-tartaggaggnttgataggtttaag-5'
SEQ ID NO: 21      3'-tartaggaggnttrataggtttaag-5'
SEQ ID NO: 22      3'-tartaggaggnttrataggnttaag-5,
SEQ ID NO: 23      3'-tartaggaggnttrataggnttaagaata-5'
SEQ ID NO: 24           3'-ggaggnttrataggnttaagaata-5'
SEQ ID NO: 25           3'-ggvggnttrataggnttaagaata-5'
SEQ ID NO: 26            3'-taggaggnttrataggnttaag-5'
SEQ ID NO: 27            3'-ggaggcttggtaggtttaaga-5'
SEQ ID NO: 28            3'-ggvggnttrataggnttaaga-5'
SEQ ID NO: 29      3'-tagtaggaggcttgataggtttaagaata-5'
SEQ ID NO: 30       3'-gtaggaggcttgataggtttaag-5'
```

In one embodiment of the present invention, the set of bi-directional primary sequencing primers includes a second primer comprising the nucleotide sequence of SEQ ID NO:16, and fragments thereof of 15 or more nucleotides, inclusive of the 3' terminus. SEQ ID NO:16 describes a set of degenerate primers that may be used as the forward primer, where R represents G or A, X represents 5-nitroindole or C, Z represents 5-nitroindole or T, and V represents A or G or C, but not T. Other variations of the above sequences may be utilized to permit detection of other HIV variants.

In another embodiment, the present invention includes a set of bi-directional primary sequencing primers that includes a second primer selected from the group consisting of SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, and SEQ ID NO:28.

In yet another embodiment, the present invention includes a set of bi-directional primary sequencing primers that includes a second primer comprising the sequence of SEQ ID NO:29, and fragments thereof of 15 or more nucleotides.

In yet another embodiment, the present invention includes a set of bi-directional primary sequencing primers includes a second primer comprising the sequence of SEQ ID NO:30.

In a yet another aspect of the present invention, the primers used to sequence the HR1 domain of HIV-1 will have a sequence selected from the group consisting of one or more of SEQ ID NO:31, SEQ ID NO:32, SEQ ID NO:33, SEQ ID NO:34, SEQ ID NO:35, and SEQ ID NO:36 (set forth below) or fragments thereof of at least 15 or more nucleotides.

```
SEQ ID NO: 31   5'-TTGGGTTCTTGGGAGCAGCAGGAAG-3'
SEQ ID NO: 32   5'-TTGGGTTCTTGGGAGCAGCAGG-3'
SEQ ID NO: 33   5'-AGTRGTGCARATGAKTTTTCCAGAG-3'
SEQ ID NO: 34   5'-GTGGTGCAGATGAGTTTTCCAGAG-3'
SEQ ID NO: 35   5'-GTGGTGCAGATGAGTTTTCCAGAGC-3'
```

SEQ ID NO:31, SEQ ID NO:32, SEQ ID NO:33 represent alternate forward primer sequences in the region to the 5' side of HR1. The primer sequence of SEQ ID NO:31 corresponds to the sequence of nucleotides 7329-7353 of SEQ ID NO:1. The primer sequence of SEQ ID NO:32 corresponds to the sequence of nucleotides 7329-7350 of SEQ ID NO:1. The primer sequence of SEQ ID NO:33 corresponds to the sequence of nucleotides 7337-7361 of SEQ ID NO:1.

SEQ ID NO:34, SEQ ID NO:35, SEQ ID NO:36 represent alternate reverse primer sequences in the region to the 3' side of HR1 (between the HR1 and HR2 domains). The primer sequence of SEQ ID NO:34 corresponds to the reverse complement of nucleotides 7563-7587 of SEQ ID NO:1 (ctctggaaaamtcatytgcacyact). The primer sequence of SEQ ID NO:35 corresponds to the reverse complement of nucleotides 7564-7587 of SEQ ID NO:1 (ctctggaaaactcatctgcaccac). The primer sequence of SEQ ID NO:36 corresponds to the reverse complement of nucleotides 7563-7588 of SEQ ID NO:1 (ctctggaaaactcatctgcaccacg).

In one embodiment of the present invention, the primer includes the nucleotide sequence of SEQ ID NO:1 and fragments thereof of 15 or more nucleotides.

In another embodiment of the present invention, the primer includes the nucleotide sequence of SEQ ID NO:31 and fragments thereof of 15 or more nucleotides.

In another embodiment of the present invention, the primer includes the nucleotide sequence of SEQ ID NO:32 and fragments thereof of 15 or more nucleotides.

In another embodiment of the present invention, the primer includes the nucleotide sequence of SEQ ID NO:33 and fragments thereof of 15 or more nucleotides.

In another embodiment of the present invention, the primer includes the nucleotide sequence of SEQ ID NO:34 and fragments thereof of 15 or more nucleotides.

In another embodiment of the present invention, the primer includes the nucleotide sequence of SEQ ID NO:35 and fragments thereof of 15 or more nucleotides.

In another embodiment of the present invention, the primers includes a set of bi-directional sequencing primers, wherein the forward primer is selected from the group consisting of SEQ ID NO:1, SEQ ID NO:31, and SEQ ID NO:32, and fragments thereof of 15 or more nucleotides, and the reverse primer is selected from the group consisting of SEQ ID NO:33, SEQ ID NO:34, and SEQ ID NO:35, and fragments thereof of 15 or more nucleotides.

The forward primer site, illustrated by SEQ ID NO:1, SEQ ID NO:31, and SEQ ID NO:32, the 3' terminal end is preferably a –G nucleotide base, and more preferably a –GG. This allows particularly strong hybridization at the 3' end of the primer and possibly enhanced sequencing results versus a primer that ends at a different location. The 3' end of the primer may extend further in the 3' direction. Due to the fact that sequence immediately following primers is generally of poor quality, the 3' end of the forward primer will preferably be located a sufficient distance from the HR1 region that the beginning of the HR1 sequence is unequivocal. Preferably, the 3' end of the forward primer will extend no further than the –AAG at the 3' end of SEQ ID NO:1, although primers extending beyond the point are contemplated, provided suitable sequence for the HR1 region can be obtained.

The 5' end of this primer could be shortened slightly, but would also change the annealing characteristics of the primer. Specifically, the 5' terminal –GG may be shortened to –G. The shorter versions (TGG-, GG-, G-) could be combined with the extension of the 3' end to further optimize the annealing (or melting temp, Tm) temperature to match other possible reverse primers.

The forward primers may be modified beyond the locations described above with appropriate modifications to the sequencing chemistry used. For instance, universal sequencing primer tails could be utilized on a nested PCR primer to move the primer inward a bit without putting the universal sequencing primer too close to the critical region. This would require that the WP primer include a universal sequencing tail as a PCR primer.

The reverse primers, illustrated by SEQ ID NO:33, SEQ ID NO:34, and SEQ ID NO:35, may also be modified in accordance with the present invention. In preferred embodiments, the 5' end of the reverse primer may be nucleotide 7564 (G) or 7563 (A). In preferred embodiments, the 3' end of the reverse primer may be nucleotide 7585 (G), 7586 (A), 7587 (G) or 7588 (C). The primer will preferably not be located any further from the HR1 region, which would place the sequence in less conserved HIV sequence positions and result in a less robust sequencing primer set. The primer will preferably not be located any closer to the HR1 region, which may not provide sufficient initial sequence immediately following the primer to allow the sequence data to be resolved before the HR1 positions are reached.

The primer combinations described above can be used in a method in accordance with the invention for a sample suspected of containing the HIV-1 virus to assess the subtype and genotype of the virus.

The method comprises the steps of treating the sample to recover viral RNA; reverse transcribing the recovered viral RNA; sequencing the reverse transcription product; and using the results of the sequencing step to establish the genotype of the tested virus. In this method, either or both of the reverse transcription step and the sequencing step are performed using primer combinations as described above. The method of the invention can include the step of performing a parallel genotyping procedure that is designed to evaluate polymorphic variations in the gp41 region of HIV, and particularly for evaluating polymorphic variations in the HR1 domain of gp41. Alternatively, the method can be utilized with a sample that has previously been the subject of a failed genotyping attempt using genotyping procedures specific for gp41.

Kits

The present invention also includes kits comprising reagents necessary and sufficient to perform the methods described above. In one aspect, the present invention is directed to a kit for detecting the presence or absence of a mutation of interest in a pathogen in a sample containing multiple quasispecies of the pathogen having mixed length polymorphisms, wherein the mutation of interest is located adjacent to the length polymorphism, comprising a first primer for sequencing a first strand of a region of a DNA template containing the mutation of interest and a second primer for sequencing a second strand of a region of the DNA template containing the mutation of interest, wherein the region defined by (i.e., including and between) the first primer and second primer excludes the length polymorphism.

In another aspect, the present invention is directed to a kit comprising one or more an oligonucleotide primers selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, and fragments thereof of 15 or more nucleotides.

In yet another aspect, the present invention is directed to a kit comprising:
(a) a forward primer selected from the group consisting of one or more of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, and fragments thereof of 15 or more nucleotides; and
(b) a reverse primer selected from the group consisting of one or more of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, and fragments thereof of 15 or more nucleotides.

In yet another embodiment, the present invention is directed to a kit comprising an oligonucleotide primer capable of generating primer extension products corresponding to the region consisting essentially of nucleotides 7329-7614 of SEQ ID NO:1, or fragments thereof of 15 or more nucleotides.

In yet another embodiment, the present invention is directed to a kit comprising an oligonucleotide primer, wherein the primer is capable of generating primer extension products corresponding to the region consisting essentially of nucleotides 7388-7549 of SEQ ID NO:1 or fragments thereof of 15 or more nucleotides.

In yet another embodiment, the present invention is directed to a kit comprising an oligonucleotide primer, wherein the primer is capable of generating primer extension products corresponding to the region consisting essentially of nucleotides 7492-7522 of SEQ ID NO:1 or fragments thereof of 15 or more nucleotides.

In yet another embodiment, the present invention is directed to a kit comprising an oligonucleotide primer, wherein the primer is selected from the group consisting of SEQ ID NO:31, SEQ ID NO:32, SEQ ID NO:33, SEQ ID NO:34, SEQ ID NO:35, and fragments thereof of 15 or more nucleotides.

In yet another embodiment, the present invention is directed to a kit comprising a primer combination comprising a set of bi-directional sequencing primers encompassing a region consisting essentially of nucleotides 7329-7614 of SEQ ID NO:1 or fragments thereof of 15 or more nucleotides.

In yet another embodiment, the present invention is directed to a kit comprising a primer combination, wherein the set of bi-directional sequencing primers encompasses a region consisting essentially of nucleotides 7388-7549 of SEQ ID NO:1 or fragments thereof of 15 or more nucleotides.

In yet another embodiment, the present invention is directed to a kit comprising a primer combination, wherein the set of bi-directional sequencing primers encompasses a region consisting essentially of nucleotides 7492-7522 of SEQ ID NO:1 or fragments thereof of 15 or more nucleotides.

In yet another embodiment, the present invention is directed to a kit comprising a primer combination, wherein the set of bi-directional primary sequencing primers comprises two or more primers selected from the group consisting of SEQ ID NO:31, SEQ ID NO:32, SEQ ID NO:33, SEQ ID NO:34, SEQ ID NO:35, and fragments thereof of 15 or more nucleotides.

In yet another embodiment, the present invention is directed to a kit comprising an primer combination, wherein the set of bi-directional sequencing primers comprises:
(a) at least one forward primer selected from the group consisting of SEQ ID NO:31 and SEQ ID NO:32, and fragments thereof of 15 or more nucleotides, and
(b) at least one reverse primer selected from the group consisting of SEQ ID NO:33, SEQ ID NO:34, SEQ ID NO:35, and fragments thereof of 15 or more nucleotides.

The following example illustrates particular embodiments of the present invention.

EXAMPLE 1

The following example illustrates bi-directional (dual strand) sequencing with a primary sequencing primer set (EC7719F, EC8311R) and a secondary sequencing primer set (WP8746F, WP8960RB and/or WP8746RC) in the HR1 region of gp41 from a clinical plasma sample exhibiting a mixed population, including a length polymorphism. A complex sequence trace obtained using only the forward strand primary sequencing primer of a nearly equal mixture with and without the length polymorphism showed inconclusive results. Routine analysis does not permit deconvolution of the resulting superimposed peaks. As demonstrated below, use of the secondary primer set produces immediately usable bi-directional results.

A representative set of combined RT-PCR and CLIP sequencing conditions was used to generate high quality sequence data using the primers:

```
EMF1      ( 5'-AGAGAAAGAGCAGAAGACAGTGGC-3'),
and

EMR1      (5'-CCTTGTAAGTCATTGGTCTTAAAGGTACC-3')
(RT-PCR primers);

EC7719F   (5'-ACCAAGGCAAAGAGAAGAGTGG-3' ),
and

EC8311R   (3'-gtaggaggcttgataggtttaag-5')
(CLIP primers);
and

WP8746F   (5'-TTGGGTTCTTGGGAGCAGCAGG-3'),

WP8960RB  (5'-GTGGTGCAGATGAGTTTTCCAGAG-3')
and/or

WP8746RC  (5'-GTGGTGCAGATGAGTTTTCCAGAGC-3')
(CLIP primers).
```

The following materials were used:

| | |
|---|---|
| RT-PCR Reagents: | TRUGENE HIV Kit |
| CLIP Reagents: | VG 30001 Core Sequencing Kit |
| RT-PCR Primers: | EMF1 (unlabelled) 30 µM |
| | EMR1 (unlabelled) 30 µM |
| CLIP Primers: | EC7719F (Cy 5.5) 3 µM |
| | EC8311R (Cy 5.0) 3 µM |
| | EC8311R (unlabelled) 3 µM |

RNA was extracted from patient plasma samples according to the package instructions in a TRUPREP Extraction Kit for viral RNA.

For RT-PCR amplification of the gp41 region, the following reagents were used:

| Number of samples | Primer stock conc. (µM) | volume(µL) required per sample |
|---|---|---|
| Master Mix I | | |
| RT-PCR Primers Forward (µL)* | 30 | 0.35 |
| RT-PCR Primers Reverse (µL)* | 30 | 0.35 |
| Nuclease free H2O (µL)** | | 14.47 |
| dNTP Solution (µL) | | 1.75 |
| DTT Solution (µL) | | 1.16 |
| RNase-Inhibitor (µL) | | 0.59 |
| TOTAL (µL)** | | 18.67 |
| Master Mix II | | |
| RT-PCR Buffer (µL) | | 11.67 |
| RNase-Inhibitor (µL) | | 0.58 |
| RT Enzyme (µL) | | 1.17 |
| DNA Polymerase (µL) | | 2.92 |
| TOTAL (µL) | | 16.34 |

Master Mix I and II were maintained on ice until use. 16 µL of Master Mix I was aliquoted to the bottom of each PCR tube. 10 µL each of the extracted RNA sample was the pipetted into the PCR plate containing Master Mix I. The tubes were then placed on the thermocycler. After 5 minutes of the single 50° C. cycle, the thermocycler was paused and 14 µL of Master Mix II was added to each well. The thermocycler program was then resumed according to the following protocol:

1× 90° C. for 2 minute

50° C. for 20 minute

Note: pause after 5 minutes of 50° C. step above to add Master Mix II

94° C. for 2 minute

37× 94° C. for 30 seconds

60° C. for 30 seconds

68° C. for 2 minute

1× 68° C. for 7 minute

4° C. hold until operator action

The resulting PCR amplification product was then sequenced as follows, using the CLIP sequencing method. First, the 7.00 µL Thermo Sequenase enzyme was diluted 10-fold with 63 µL enzyme dilution buffer, to a total volume of 70.00 µL. 11.50 µL of labeled EC8311R (3 µL) reverse primer was then diluted 50% with 11.50 µL of unlabeled EC8311R (3 µL) reverse primer, to a total volume of 23.00 µL. The gp41 CLIP Master Mix was then prepared as follows:

| gp41 CLIP Master Mix | volume(μL) required Master Mix per sample |
| --- | --- |
| Sequencing Buffer (μL) | 2.75 |
| EC7719F (3 uM) (μL) | 1.38 |
| EC8311R primer mix | 1.38 |
| DNA (μL) | 0.00 |
| DMSO (μL) | 0.00 |
| dH2O (μL) | 8.80 |
| 1:10 diluted Thermo Sequenase (μL) | 4.40 |
| Total (μL) | 18.71 |

17 μL of CLIP Master Mix was added to 5 μL of each amplification product to be sequenced. 3 μL of the termination mix A, C, G, T was then pipetted into each sequencing tube 5 μL of the Master Mix/amplification product was pipetted into each sequencing tube containing the termination mixes. The mixes were then sequenced using the following CLIP Sequencing Thermocycling program:

| 1x | 94° C. for 5 minute |
| --- | --- |
| (30) x | 94° C. for 20 seconds |
|  | 60° C. for 20 seconds |
|  | 70° C. for 1.5 minute |
| 1x | 70° C. for 5 minute |
|  | 4° C. hold |

Once sequencing was complete, 6 μL stop loading dye was added into each tube. Samples were heated at 94° C. for 2 min, quenched on ice and mixed well by gentle vortexing. 24 were loaded into each well of the Microcel™ cassette. The TRU-GENE protocol for LRTower setup and loading, as provided by the manufacturer, was then followed for automated DNA sequencing, using Microcel 500 and 6% Surefill, with 2000V, 50% laser power and 70 minute run time.

Table 1 and Table 2 below show analysis of results of sequencing the HR1 and HR2 regions combined (Table 1) and sequencing the HR1 region alone (Table 2). As shown in Table 1, the "ambiguous matches" column matches at least one base or code with an ambiguous base-call at the position in each of the FASTA files.

TABLE 1

| HR1 and HR2 Regions Combined | | | | | |
| --- | --- | --- | --- | --- | --- |
| Sample | Ambiguous Mismatches | All Mismatches | Strictly Mismatched | Alignment Length | % Consistency |
| 22871.msf | 26 | 26 | 0 | 486 | 100.0 |
| 28942.msf | 22 | 23 | 1 | 485 | 99.8 |
| 35794.msf | 30 | 32 | 2 | 487 | 99.6 |
| 37047.msf | 31 | 34 | 3 | 487 | 99.4 |
| 61919.msf | 7 | 7 | 0 | 486 | 99.4 |
| 62290.msf | 22 | 23 | 1 | 494 | 99.8 |
| 62291.msf | 15 | 15 | 0 | 488 | 100.0 |
| 62292.msf | 11 | 11 | 0 | 486 | 100.0 |
| 62293.msf | 17 | 17 | 0 | 486 | 100.0 |
| 62294.msf | 9 | 10 | 1 | 487 | 99.8 |
| 62295.msf | 43 | 43 | 0 | 486 | 100.0 |
| 62316.msf | 14 | 14 | 0 | 489 | 100.0 |
| 62317.msf | 11 | 13 | 2 | 485 | 99.6 |
| 62423.msf | 10 | 10 | 0 | 486 | 100.0 |
| 62424.msf | 10 | 11 | 1 | 486 | 99.8 |
| 63009.msf | 10 | 12 | 2 | 486 | 99.6 |

TABLE 1-continued

| HR1 and HR2 Regions Combined | | | | | |
| --- | --- | --- | --- | --- | --- |
| Sample | Ambiguous Mismatches | All Mismatches | Strictly Mismatched | Alignment Length | % Consistency |
| 63680.msf | 88 | 94 | 6 | 492 | 98.8 |
| pc.msf | 7 | 9 | 2 | 486 | 99.6 |

The above data demonstrates that primers encompassing the HR1 and HR2 regions of HIV-1 are able to obtain sequence data for a broad range of HIV variants.

Table 2 demonstrates that in preferred aspects of the invention, in which the primers encompass the HR1 region alone, fewer ambiguous matches in the HR1 region result in fewer editing steps and higher overall consistency.

TABLE 2

| HR1 Region Only | | | | | |
| --- | --- | --- | --- | --- | --- |
| Sample | Ambiguous Mismatches | All Mismatches | Strictly Mismatched | Alignment Length | % Consistency |
| 22871.msf | 2 | 2 | 0 | 273 | 100.0 |
| 28942.msf | 9 | 9 | 2 | 272 | 100.0 |
| 35794.msf | 19 | 21 | 1 | 273 | 99.3 |
| 37047.msf | 19 | 20 | 0 | 273 | 99.6 |
| 61919.msf | 3 | 3 | 0 | 273 | 100.0 |
| 62290.msf | 5 | 5 | 0 | 273 | 100.0 |
| 62291.msf | 0 | 0 | 0 | 273 | 100.0 |
| 62292.msf | 2 | 2 | 0 | 273 | 100.0 |
| 62293.msf | 2 | 2 | 0 | 273 | 100.0 |
| 62294.msf | 4 | 4 | 0 | 274 | 100.0 |
| 62295.msf | 27 | 27 | 0 | 273 | 100.0 |
| 62316.msf | 1 | 2 | 0 | 273 | 100.0 |
| 62317.msf | 5 | 7 | 2 | 272 | 99.3 |
| 62423.msf | 3 | 3 | 0 | 273 | 100.0 |
| 62424.msf | 0 | 0 | 0 | 273 | 100.0 |
| 63009.msf | 3 | 3 | 0 | 273 | 100.0 |
| 63680.msf | 45 | 45 | 0 | 273 | 100.0 |
| pc.msf | 0 | 0 | 0 | 273 | 100.0 |

With reference to a specific patient sample, sequence traces from sample 28942 were generated using both the EC primer set and the WP primer set. The sequence data generated with only the EC primer set resulted in sequence data that was readable and could be confirmed in unreadable from one direction, resulting in ambiguous results that could not be confirmed. When sample 28942 was analyzed with the WP primer set, however, the ambiguous data was confirmed with the antisense strand sequence.

The above data demonstrates that sequencing a region consisting essentially of the HR1 domain, using the primers of the present invention, result in significantly fewer ambiguities and mismatches, and improved accuracy and consistency of sequencing results. For example, the following examples of HIV-1 gp41 sequencing data generated in the area of particular interest for enfuvirtide (FUZEON™ or T-20) treatment associated resistance mutations (HR1) include data with the standard design primers (EC) and the new primers (WP). In general any mixed length polymorphism mutation that occurs between one of the outer primers and the mutations of interest causes the sequence quality to decline due to overlayed and out of frame sequences being generated. The primers of the present invention circumvent the problem and produce high quality bidirectional sequence data in the area of interest, allowing antisense strand confirmation of any mutations that occur in HR1.

What is claimed is:

1. A primer combination comprising a set of bi-directional sequencing primers encompassing a region comprising the HR1 and HR2 domains of HIV-1, wherein the primer combination comprises:
   (a) a forward primer selected from the group consisting of: SEQ ID NO:2, SEQ ID NO:3, SEQ ID NO:4, SEQ ID NO:7, SEQ ID NO:8, SEQ ID NO:10, SEQ ID NO:11, SEQ ID NO:12, SEQ ID NO:13; and
   (b) a reverse primer comprising nucleotides 1-20 of SEQ ID NO:28.

2. The primer combination according to claim 1, further comprising SEQ ID NO: 31 and SEQ ID NO: 34.

3. The primer combination of claim 2 further comprising, SEQ ID NO:32, SEQ ID NO:33 and SEQ ID NO:35.

4. A method for detecting the presence or absence of a mutation of interest in the nucleic acid of a pathogen, wherein the mutation of interest is located adjacent to a length polymorphism defining multiple quasispecies of the pathogen, comprising:
   a) obtaining from the patient sample a double-stranded DNA template encompassing the mutation of interest;
   b) sequencing a first strand of a region of the DNA template containing the mutation of interest;
   c) sequencing a second strand of a region of the DNA template containing the mutation of interest, wherein the region of the DNA template sequenced that is common to the first strand and second strand excludes the length polymorphism, wherein the sequencing step comprises providing sequencing primers according to claim 1; and
   d) comparing the sequence of the first strand with the sequence of the second strand to obtain complementary strand confirmation of the sequence of the mutation of interest.

5. A method according to claim 4, wherein the pathogen is HIV-1.

6. The method according to claim 4, wherein the mutation of interest is located in the HIV-1 envelope glycoprotein gp41.

7. The method of claim 6, wherein the mutation of interest is located within position 36-45 of gp41.

8. The method according to claim 4, wherein the region of the DNA template sequenced that is common to the first strand and second strand and excludes the length polymorphism consisting essentially of nucleotides 7329-7614 of SEQ ID NO:1.

9. The method according to claim 4, wherein the region of the DNA template sequenced that is common to the first strand and second strand and excludes the length polymorphism consisting essentially of nucleotides 7388-7549 of SEQ ID NO:1.

10. The method according to claim 4, wherein the region of the DNA template sequenced that is common to the first strand and second strand and excludes the length polymorphism consisting essentially of nucleotides 7492-7522 of SEQ ID NO:1.

11. The method according to claim 4, wherein the sequence is determined using primers comprising SEQ ID NO:31 or SEQ ID NO: 34 or combinations thereof.

12. A kit for detecting the presence or absence of a mutation of interest in a pathogen in a sample containing multiple quasispecies of the pathogen having mixed length polymorphisms, wherein the mutation of interest is located adjacent to the length polymorphism, comprising a first primer for sequencing a first strand of a region of a DNA template containing the mutation of interest and a second primer for sequencing a second strand of a region of the DNA template containing the mutation of interest, wherein the region defined by the first primer and second primer excludes the length polymorphism and wherein the forward primer is selected from the group consisting of: SEQ ID NO:2, SEQ ID NO:3, SEQ ID NO:4, SEQ ID NO:7, SEQ ID NO:8, SEQ ID NO:10, SEQ ID NO:11, SEQ ID NO:12, SEQ ID NO:13 and wherein the kit further comprises SEQ ID NO:33 and SEQ ID NO:35.

* * * * *